United States Patent [19]

Carnmelm et al.

[11] 4,053,632
[45] * Oct. 11, 1977

[54] COMPOUNDS OF SPIRO-AMINE TYPE AND METHODS FOR THEIR USE

[75] Inventors: Bernt Sigfrid Emanuel Carnmelm, Sodertalje; Tomas DePaulis, Gnesta; Suante Bertil Ross, Sodertalje; Sten Ingvar Rämsby, Sodertalje; Nil-Erik Stjernström, Sodertalje; Sven-Oje Ögren, Sodertalje, all of Sweden

[73] Assignee: Astra Lakemedel Aktiebolag, Sodertalje, Sweden

[*] Notice: The portion of the term of this patent subsequent to Sept. 9, 1992, has been disclaimed.

[21] Appl. No.: 536,810

[22] Filed: Dec. 27, 1974

Related U.S. Application Data

[63] Continuation-in-part of Ser. No. 256,945, May 25, 1972, Pat. No. 3,904,691.

[30] Foreign Application Priority Data

June 11, 1971 Sweden ................................. 717630

[51] Int. Cl.$^2$ ............................................. A01N 9/20
[52] U.S. Cl. ..................................... 424/316; 560/27; 260/501.12; 260/501.1; 424/515 R; 260/515 A; 260/644 N; 260/558 R; 260/562 P; 260/566 A; 260/566 B; 260/566 AE; 260/578; 260/590 C; 260/611 F; 424/330
[58] Field of Search ..................... 260/576, 578, 501.1; 424/316, 330

[56] References Cited
PUBLICATIONS

Basger, "Medicinal Chemistry," 2nd Ed., pp. 44–45, (1960).

Primary Examiner—Robert V. Hines
Attorney, Agent, or Firm—Brumbaugh, Graves, Donohue & Raymond

[57] ABSTRACT

Compounds of the formula

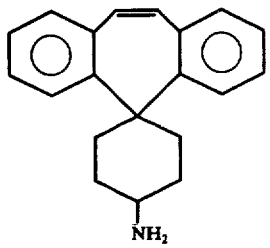
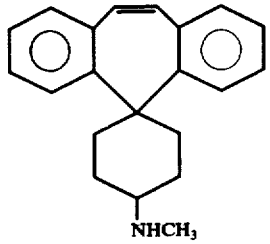
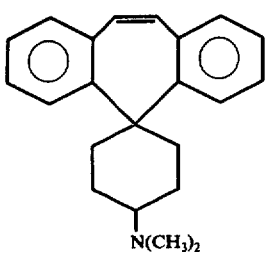
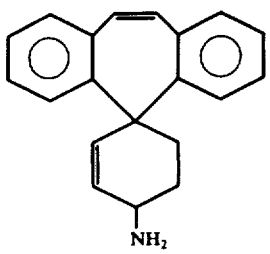

-continued

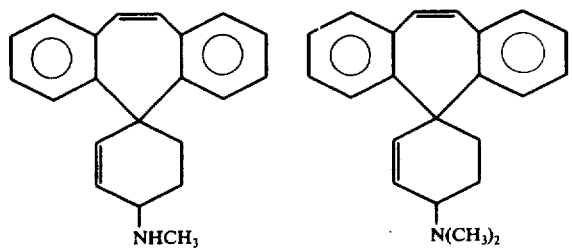

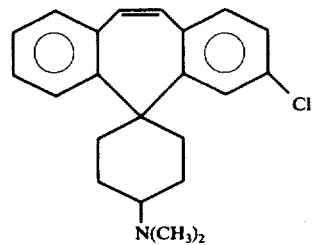

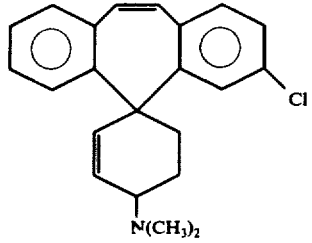

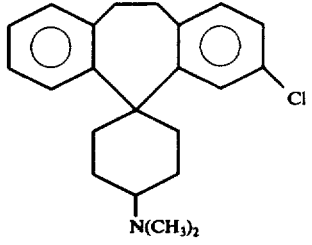

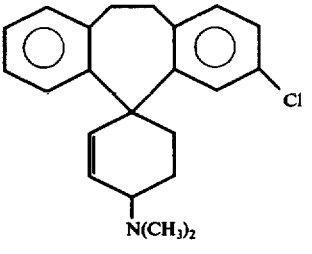

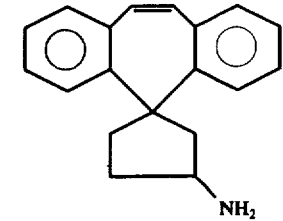

and pharmaceutically acceptable salts thereof; processes for their preparation; intermediates useful for their preparation; pharmaceutical preparations containing at least one of these compounds; and the use thereof as a tranquilizing or neurolentic agent.

19 Claims, 1 Drawing Figure

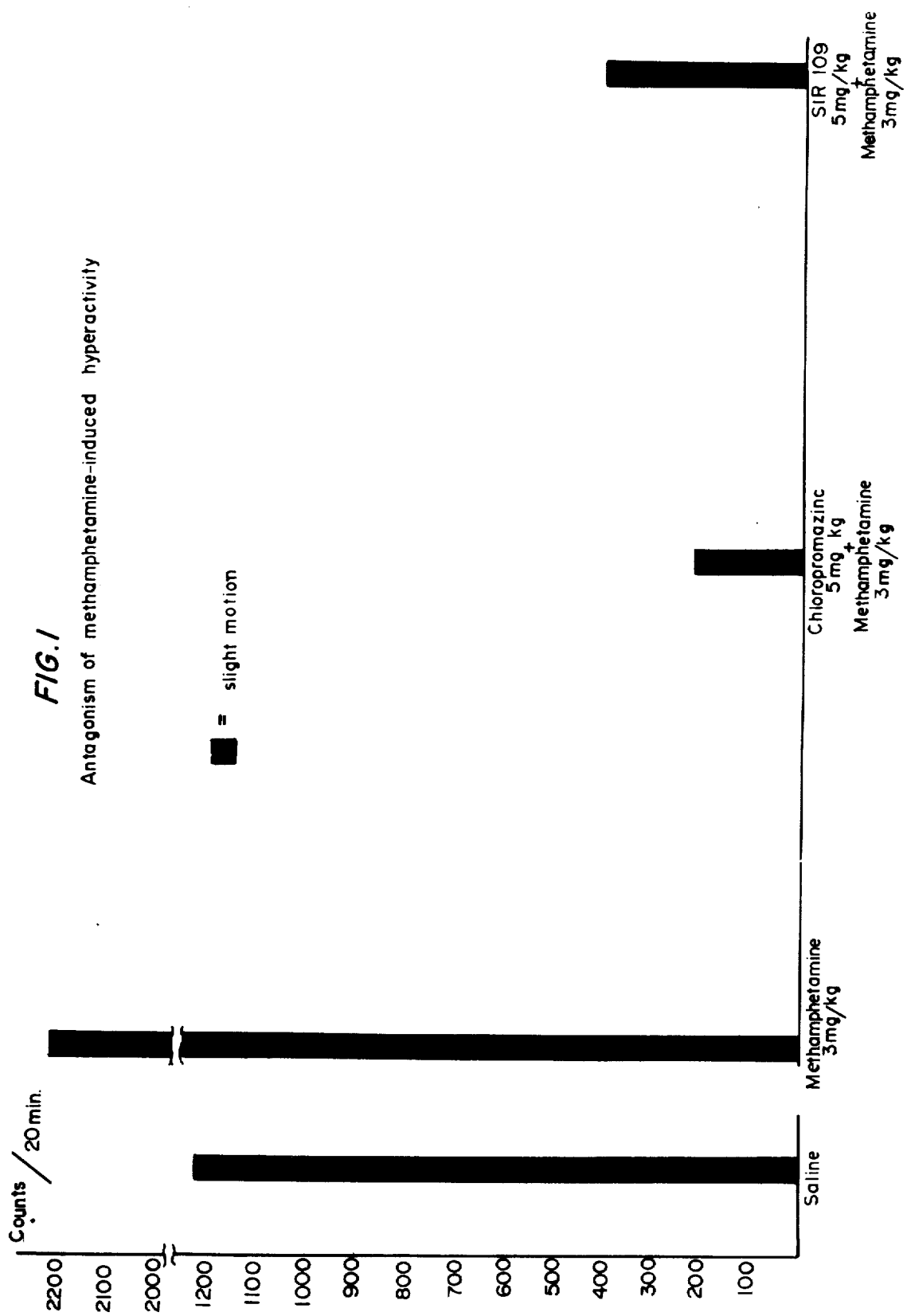

COMPOUNDS OF SPIRO-AMINE TYPE AND METHODS FOR THEIR USE

This application is a division and continuation-in-part of our copending application Ser. No. 256,945 filed May 25, 1972 now U.S. Pat. No. 3,904,691, issued Sept. 9, 1975.

This invention relates to new compounds of the spiro-amine type and methods for their preparation. The invention also relates to the preparation of pharmaceutical preparations containing such compounds and to methods for the pharmacological use of the compounds. Further this invention relates to certain intermediates necessary for the preparation of the end products.

The main object of the invention is to provide compounds having neuroleptic or tranquilizing properties.

Depressions are considered to depend on changes in the biochemical processes of the brain which control the mood. The nature of this biochemical deficiency is largely unknown but in depressive states there is evidence for a decreased activity of monoaminergic brain neurons. The monoamines, noradrenaline (NA), dopamine (DA) and 5-hydroxytryptamine (5-HT), are of great interest in this respect.

It has been demonstrated that NA, DA and 5-HT are localized in three different types of neurones and may function as transmittors in the central nervous system. The monoamines are stored in special structures, granules, situated in enlargements of the nerve endings, varicosities. The varicosity is separated from the effector neuron by a space, the synaptic cleft or spatium. As a result of a nerve stimulation the transmittor is released from the granule into the synaptic cleft and reaches the receptor of the effector neuron and generates a nerve impulse. After impulse generation the amines are inactivated by mainly two mechanisms: a re-uptake mechanism at the cell membrane and enzymatic conversion by catechol-0-methyltransferase to form methylated metabolites. There is also an inactivating enzyme within the varicosities, monoamine oxidase (MAO), that is stored in the mitochondria and inactivates the amines intracellularly.

When MAO-inhibitors are administered, an increased amount of transmittor substance becomes available for release at the nerve ending.

Another way of increasing the amine levels at the receptor is exerted by the tricyclic antidepressants. It has been shown that this type of compounds inhibits the re-uptake mechanism of NA and 5-HT, and the antidepressive action is assumed to be related to the uptake inhibition of NA and 5-HT.

The over all clinical effect of the tricyclic antidepressants consists according to Kielholz (Deutsch Med. Wschr. 93, 1968) of three main components in various proportions:

1. Psychomotor activating or increase in drive
2. Elevation of mood
3. Relief of anxiety It has been proposed that the correlation between the clinical effects and the biochemical changes in the adrenergic neurones might be that the NA neurones are involved in psychomotor activity and the 5-HT-neurones are involved in the elevation of mood. The third component, relief of anxiety, may be caused by blockade of the NA and DA receptors, but probably not the 5-HT receptors. However, it should be pointed out that these theories are much simplified.

A compound frequently used for controlling depressions is imipramine (Tofranil ®)

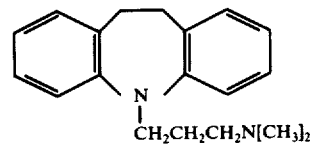

This compound is both mood elevating and psychomotor activating, but it possesses several disadvantages. It is anticholinergic and causes anticholinergic symptoms such as dryness of the mouth, tremor, tachycardia and sweating. In higher doses it can provoke serious heart arrhythmias and in normal doses it can cause toxic interactions in persons with heart failures. Furthermore, another drawback with treatment with imipramine is the late onset of the antidepressive effect which effect is observable first after 3 weeks of treatment.

According to the present invention it has now been found that compounds selected from the group consisting of

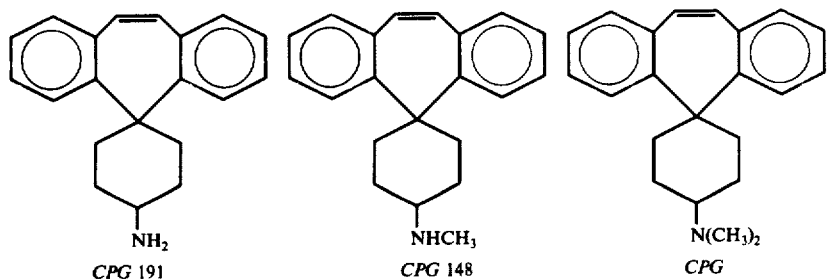

-continued

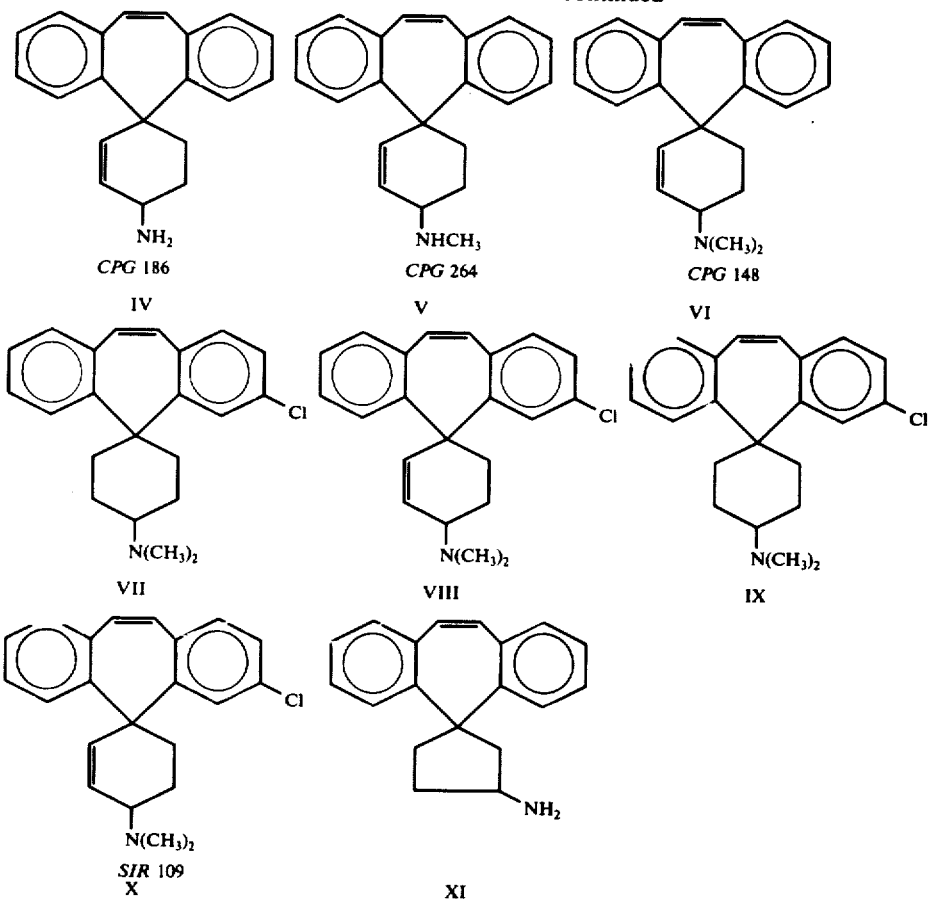

and pharmaceutically acceptable salts thereof, are useful as tranquilizing or neuroleptic agents having less unwanted side effect than similar compounds known in the art.

Compounds described above which contain an asymmetric carbon atom exist in the form of optically active forms, and can be resolved into their optical antipodes by well known methods such as by using optically active acids such as tartaric acid, camphor-10-sulphonic acid, dibenzoyl tartaric acid and the like.

Some of the compounds described above can exist as stereo isomers, which forms constitute a further aspect of this invention. Mixtures of such isomers can be separated by methods known to the state of the art.

The compounds described above can be used as mixtures of the above mentioned isomeric forms or in the form of pure isomers.

FIG. 1 is a graphical illustration of the activity of a composition of the present invention in blocking the methamphetamine induced hyperactivity in mice.

The compounds of the formulas I-XI above can be prepared by reactions known per se from intermediates of the formulas

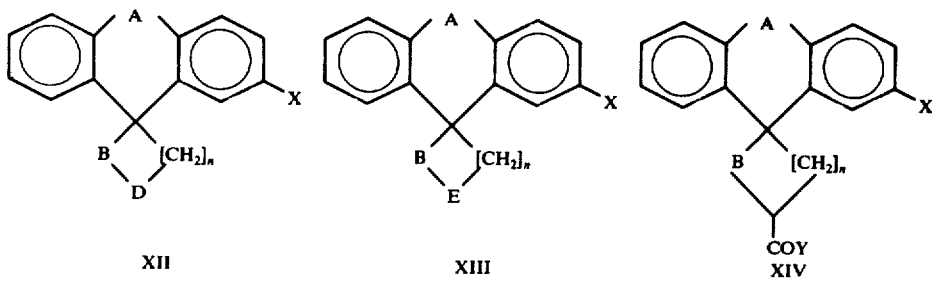

wherein A and B are the same or different and each representing —CH$_2$CH$_2$— or —CH = CH—, $n$ is an integer 1,2 or 3, X is a hydrogen atom or Cl and >D is selected from the group consisting of the radicals >C = O,

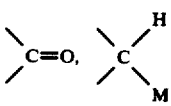

wherein M is Cl, Br,I or OSO$_2$R″ and wherein R″ is a hydrogen atom, an alkyl group with 1 to 5 carbon atoms such as methyl or an aryl group, such as phenyl or tolyl, >E is selected from the group consisting of the radicals >C = NOR″, >C = NOCOR″, >C = NOSO$_2$R″, >C = NR,

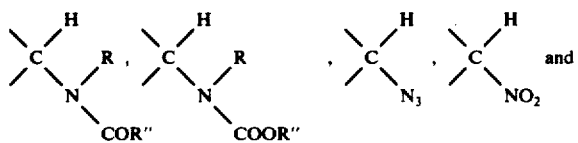

>C = N-NH-R'' in which radicals R'' has the meaning given above and R is a hydrogen atom or a methyl group, and Y is selected from the group consisting of the radicals —OH, —NH$_2$, —Cl, —Br, —I, —OCH$_3$ and —OC$_2$H$_5$.

The intermediates described above fall within the embodiment of this invention.

The intermediates of the formulas XII, XIII and XIV which are specially preferred have the formula

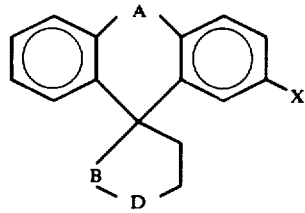

wherein A, B and X have the meaning defined above and >D is >C = O,

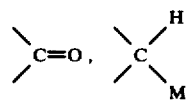

wherein M is Cl, Br, I or OSO$_2$CH$_3$, >C = NOH and

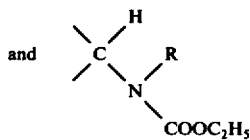

wherein R is a hydrogen atom or a methyl group.

The compounds of this invention with the formulas I-XI may be prepared according to several different methods.

A. Reaction of a compound of the formula

XII

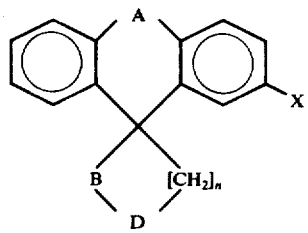

wherein A, B, X, n and D have the meaning defined above, with a compound of the formula

R''' NRR'     XV wherein R and R' are the same or different and each representing a hydrogen atom or a methyl group and R''' is a hydrogen atom, an acylic group or a sulphonylic group, gives a compound of the formulas I-XI.

This reaction may be carried out in the presence of a reducing agent. In the cases where an intermediate acylic derivative or the like is obtained, hydrolysis is necessary to obtain the compounds of the formulas I-XI.

An example of this type of reaction is the process wherein a compound of the formula

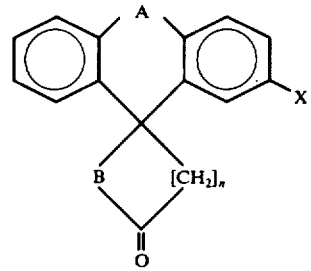

Therein, A, B, X and n have the meaning given above, is reacted with a compound of the formula

R''' NRR' wherein R and R' have the meaning given above and R''' is a formyl group or a hydrogen atom, in formic acid as reducing agent (Leuchart - Wallach reaction), to give compounds of the formula I-XI. Other suitable reductive agents are for instance catalytically activated gaseous hydrogen or hydrides as NaBH$_3$CN.

B. Amines of the formulas I-XI may also be obtained by reducing a compound of the formula

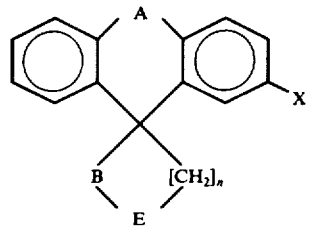

wherein A, B, E, n and X have the meaning given above. Suitable reducing agents are hydrogen in status nascendi (sodium and some alcohol; zinc and acetic acid), catalytically activated hydrogen gas (Pt, Pd, Ni are appropriate catalysts) and hydrides.

C. The amines of the formula I-XI are obtained e.g. when compounds of the formula

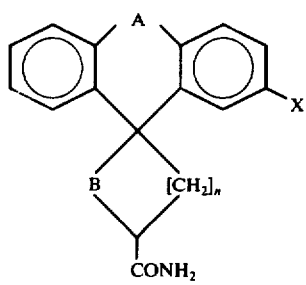

wherein A, B, X, and n have the meaning defined above, are treated with hypobromite or hypochlorite according to the conditions of the Hofmann reaction, which gives a primary amine, and if the secondary or tertiary amine is desired converting the obtained primary amine in ways known per se to the corresponding secondary or tertiary amine.

D. The amines of the formula I–XI are obtained when compounds of the formula

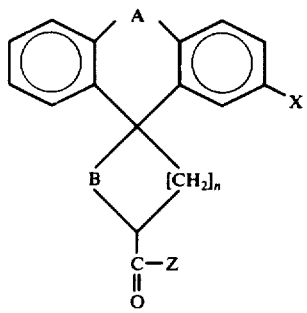

wherein A, B, X, and n have the meaning given above, and Z is a hydroxy group, a halogen group, e.g. chlorine or another acid residue, e.g. an acid anhydride, are treated with hydrazoic acid ($NH_3$) or an inorganic salt thereof according to the conditions of the Schmidt reaction, which gives a primary amine, and if a secondary or tertiary amine is desired converting the obtained primary amine in ways known per se to the corresponding secondary or tertiary amine.

In the cases in the methods A–D where an intermediate acylic derivative or the like is obtained, hydrolysis is necessary to obtain the compounds of the formulas I–XI.

Both organic and inorganic acids can be employed to form non-toxic pharmaceutically acceptable acid addition salts of the compounds of this invention. Illustrative acids being sulfuric, nitric, phosphoric, hydrochloric, citric, acetic, lactic, tartaric, pamoic, ethanedisulfonic, sulfamic, succinic, cyclohexylsulfamic, fumaric, maleic and benzoic. These salts are readily prepared by methods known to the art.

In clinical practice the compounds of the present invention will normally be administered orally or by injection, in the form of pharmaceutical preparations comprising the active ingredient either as a free base or as a pharmaceutically acceptable non-toxic, acid addition salt, e.g. the hydochloride, lactate, acetate, sulfamate, and the like, in association with a pharmaceutically acceptable carrier. Accordingly, terms relating to the novel compounds of this invention, whether generically or specifically, are intended to include both the free amine base and the acid addition salts of the free base, unless the context in which such terms are used, e.g. in the specific examples, would be inconsistent with the broad concept. The carrier may be a solid, semisolid or liquid diluent or capsule. These pharmaceutical preparations constitute a further aspect of this invention. Usually the active substance will constitute between 0.1 and 95% by weight of the preparation, more specifically between 0.5 and 20% by weight for preparation intended for injection and between 2 and 50% by weight for preparations suitable for oral administration.

To produce pharmaceutical preparations containing a compound of the invention in the form of dosage units for oral application, the selected compound may be mixed with a solid fine grain carrier, e.g., lactose, saccharose, sorbitol, mannitol, starches such as potato starch, corn starch or amylopectin, cellulose derivatives, or gelatin and a lubricant such as magnesium stearate, calcium stearate, polyethylene glycol waxes, and the like, and then compressed to form tablets. If coated tablets are required, the cores, prepared as described above, may be coated within a concentrated sugar solution which may contain, e.g., gum arabic, gelatin, talcum, titanium dioxide, and the like. Alternatively, the tablet can be coated with a lacquer dissolved in a readily volatile organic solvent or mixture of organic solvents. Dyestuffs may be added to these coatings in order to readily distinghish between tablets containing different active substances of different amounts of the active compound.

For the preparation of soft gelatin capsules (pearl-shaped closed capsules) consisting of gelatin and, for example, glycerol or similar closed capsules, the active substances may be admixed with a vegetable oil. Hard gelatin capsules may contain granulates of the active substance in combination with solid, fine grain carriers such as lactose, saccharose, sorbitol, mannitol, starches (e.g. potato starch, corn starch or amylopectin), cellulose derivatives or gelatin.

Liquid preparations for oral application may be in the form of syrups or suspensions, for example, solutions containing from about 0.2% to about 20% by weight of the active substance herein described, the balance being sugar and a mixture of ethanol, water, glycerol, and propyleneglycol. Optionally such liquid preparations may contain colouring agents, flavouring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10 % by weight. These solutions may also contain stabilizing agents and/or buffering agents and may conveniently be provided in various dosage unit ampoules.

In therapeutical treatment the suitable diurnal doses of the compounds of the invention are 5–500 mg of oral application, preferentially 50–250 mg and 1–100 mg for parenteral application, preferentially 10–50 mg.

The following examples will further illustrate the invention.

Preparation of intermediates

EXAMPLE 1.

Preparation of spiro [2-cyclohexene-1,5′(5′H)-dibenzo[a,d]cycloheptene]-4-one a)                                                       CPG 138

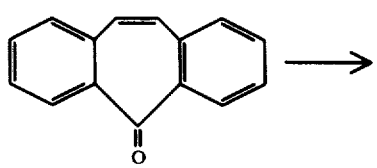

XVI

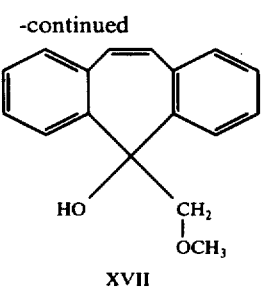

XVII 48.6 g of magnesium turnings (2.0 mole) covered with 100 ml of dry tetrahydrofuran were treated with 2.5 g of mercuric chloride. When the liquid showed a grey tint after about 5 minutes stirring there was started a dropwise addition of 150 ml of freshly distilled chlorodimethylether (2.0 mole) in 150 ml of tetrahydrofuran. When the temperature began to rise the mixture was quickly cooled to $-10°$ C, the addition continued at $-10° - 5°$ C and was completed in about 2 hours. After further stirring for 15 minutes a solution of 206g of the ketone XVI (1.0 mole) (commercially available) in 1 l of tetrahydrofuran was slowly added at $-10°$ C. The mixture turned first violet and then rather dark. It was allowed to reach room temperature slowly (1-2 hours) and finally heated at 50° C for 30 minutes. The now faintly yellow mixture was cooled and poured into 1.5 l of ice-water containing 200 g of ammonium chloride, an oil separated and was taken up in ether, the aqueous phase was extracted with ether and the combined ethereal layers ($\sim$2.5 l) were washed with water until neutral to litmus. Drying ($Na_2SO_4$) and evaporation gave 226 g of slightly yellow crystals. After recrystallization from $\sim$800 ml of ethanol 203 g (yield 81%) of the enolether XVII was secured as colourless crystals. M.p. 86°-87° C.

b)                    CPG 139

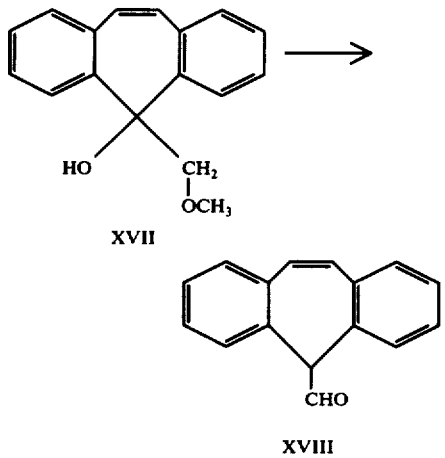

166 g (0.66 mole) of the glycolether XVII was rapidly added with stirring at 50° C to 350 ml of formic acid (98%). The solution immediately turned red but after three minutes the colour had disappeared again. The temperature was raised to 60° C in 10 minutes, 10 ml of sulfuric acid (0.1 N) added and the mixture cooled to room temperature in an ice bath. Then it was slowly poured with stirring into 1.5 kg of ice water containing 200 ml of sulfuric acid (1 M). After two hours of stirring the precipitated colourless crystals were collected, washed with water and air dried giving 110 g of crude aldehyde XVIII. After recrystallization from 500 ml of a mixture of diethyl ether and diisopropyl ether the product weighed 71 g (yield 49%) and melted at 109.5°-110.5°.

c)                    CPG 140

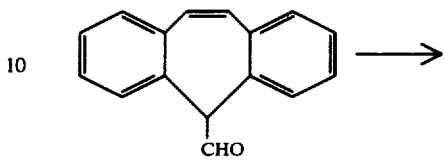

XVIII

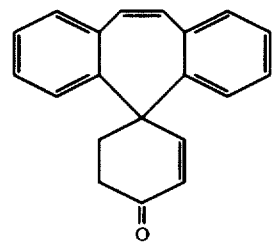

XIX 33 g of the aldehyde XVIII and 13.2 ml of freshly distilled methyl vinyl ketone were dissolved in 250 ml of dry tetrahydrofuran and 10 ml of ethanolic potassium hydroxide (10% w/v) was added slowly during about one hour at 10° C under nitrogen. After stirring at ambient temperature for another three hours there was added 1 l of diethyl ether and 200 ml of water and the mixture was neutralised with dilute hydrochloric acid. Washing the etheral layer with water, drying ($Na_2SO_4$) and evaporation gave 40.8 g of a hard, semicrystalline, yellow gum. Some tests with TLC showed benzene to be a good developing solvent. All the yellow material was chromatographed on a column (1kg of silicic acid, 0.2-0.5 mm) with benzene as eluant. Some of the starting material was recovered from the first fractions, then 26 g of the spiroketone XIX was obtained, the rest on the column was probably of polymeric nature. Crystallization from 500 ml of ethanol gave 18.6 g (yield 44%) of the ketone as colourless crystals, m.p. 138°-139° C.

EXAMPLE 2.

Preparation of spiro[2-cyclohexene-1.5′(5′H)-dibenzo[a,d]cycloheptene]-4-one oxime

CPG 169

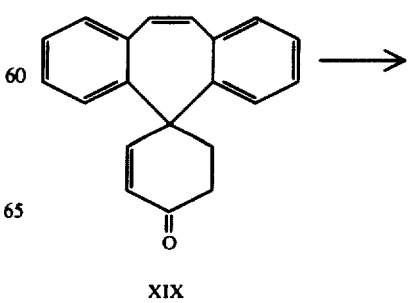

XIX

-continued

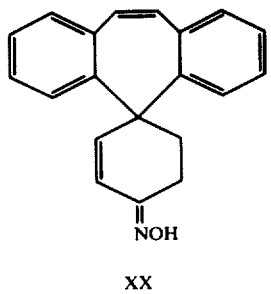

XX

A mixture of 10 g of XIX (37 mmole), 10 g of hydroxylamine hydrochloride (144 mmole), 100 ml of dry pyridine, and 100 ml of absolute ethanol was refluxed for 45 minutes. The clear solution was evaporated to dryness in vacuo and the residue crystallised from ethanol water (3+1) and then from absolute ethanol. The colourless crystals of compound XX with m.p. 85°–87° weighed 7.6 g, yield 65%.

EXAMPLE 3.

Preparation of 4-(ethoxycarbonylamino)spiro[2-cyclohexene-1,5′(5′H)-dibenzo[a,d]cycloheptene]

CPG 263

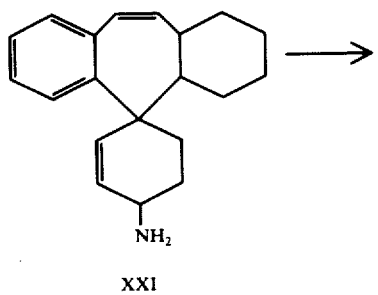

XXI

XXII 2.2 g of ethyl chloroformate (20 mmole) was added dropwise for 10 min with ice cooling and efficient stirring to a solution of 3.2 g of the amine XXI (12 mmole) in 20 ml of chloroform in the presence of 10 ml of sodium hydroxide solution (2M). After further 10 minutes stirring the chloroform phase was washed with water, dried (Na$_2$SO$_4$) and evaporated. The residue crystallized when triturated with isopropyl ether giving the urethane XXII as colourless crystals, 3.16 g (yield 78%) m.p. 153°–154° C from isopropyl ether.

EXAMPLE 4.

Preparation of spiro[cyclohexane-1,5′(5′H)-dibenzo[a,d]cycloheptene]-4-one

CPG 145

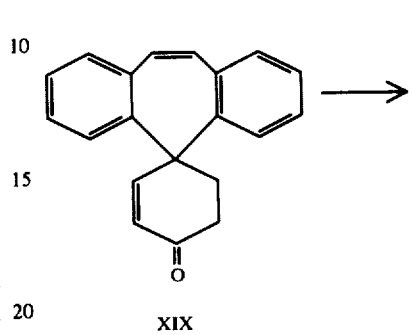

XIX

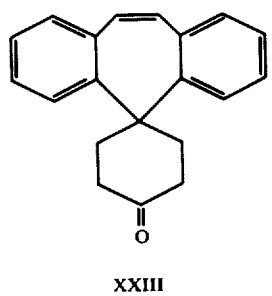

XXIII 17.0 g of the cyclohexenone XIX in 200 ml of glacial acetic acid was hydrogenated over 3.0 g of a palladium catalyst (5% on carbon) at ambient temperature and pressure. After about one hour the requisite amount of hydrogen (1.4 l) had been consumed and the uptake ceased. A precipitate had formed which was dissolved on warming. The catalyst was filtered off hot and the solution chilled to give crystals of the cyclohexanone XXIII. Recrystallization from 400 ml of ethanol gave 12.3 g (yield 72%) of the pure ketone m.p. 164°–165° C.

EXAMPLE 5.

Preparation of 4-(formylmethylamino)spiro[cyclohexane-1,5′(5′H)-dibenzo[a,d]cycloheptene]

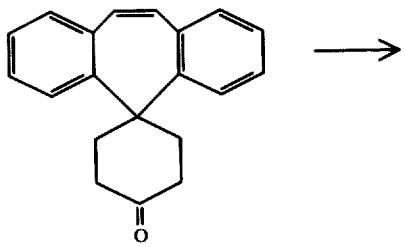

XXIII

XXIV

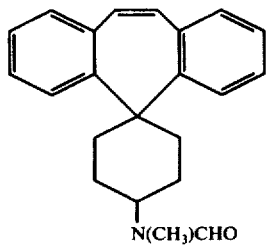

Methylammonium formate (from 4 ml of methylamine and 0.8 ml of formic acid) together with a suspension of 2 g of the spiroketone XXIII in 5 ml of N-methylformamide was heated under reflux for 5 hours, bath temperature 150° C. The reaction mixture was dissolved in benzene and washed with diluted hydrochloric acid and water. After drying (Na₂SO₄) the benzene was evaporated giving a product XXIV (1.86 g) which was recrystallized from 15 ml of methanol yielding 1.2 g (52 %) of colourless crystals melting at 188°-190° C.

EXAMPLE 6.

Preparation of 3-chloro-10,11-dihydrospiro [5H-dibenzo[a,d]cycloheptane-5,1'-cyclohexane-4'-one (22)]

a)

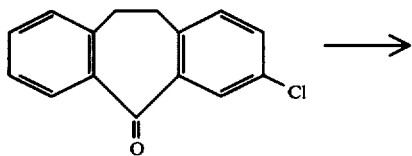

3.9 g of magnesium turnings and a few crystals of iodine were covered with 10 ml of dry formaldehyde dimethylacetal (methylal) under nitrogen and heated to reflux until the iodine colour had disappeared. After cooling to room temperature 2 mg of mercuric chloride was added and 15 minutes later a dropwise addition of 12 g of chloromethylether in 20 ml of methylal was started. The addition was done at ambient temperature until the reaction had started and then at about − 10° C. It took in all about one hour and the mixture was then stirred for another hour at −5° - -10° C. 20 g of the chloroketone XXV [prepared according to Winthrop et al., J. Org. Chem., 27, 230 (1962)] dissolved in 45 ml of methylal was added dropwise, still with cooling. The mixture turned red and finally deep violet. During an additional hour of stirring it was allowed to reach room temperature. 20 ml of saturated solution of ammonium chloride was added and the pH adjusted to 1-2 with hydrochloric acid (2M) and the mixture extracted with ether (3 × 100 ml).

The combined extracts were washed with saturated sodium carbonate solution, dried (Na₂SO₄) and evporated in vacuo. The oily residue was distilled under nitrogen at reduced pressure, yielding 21.3 g of the glycol ether XXVI (89%) as a slightly yellow highly viscous oil, b.p. 186°-187° /0.05 mm. Hg.

b)

78 g of the glycol ether XXVI was rapidly added with stirring to 600 ml of boiling, formic acid (98%). After 5 minutes sulfuric acid (1M) was added dropwise to the green solution until a small amount of oil separates (∼ 100 ml), and the boiling was continued for further 15 minutes. On cooling an oil separated which crystallizes on cooling. The greenich solid material was collected (57 g) and crystallized from benzene- petroleum-ether giving the aldehyde XXVII as colourless crystals (52 g; 74%) m.p. 147°-148° C.

c)

To a solution of 5.15 g of the aldehyde XXVII and 1.68 g of methyl vinyl ketone in a mixture of 45 ml of dry tetrahydrofuran and 5 ml of hexamethylphosphorictriamide was added dropwise under nitrogen 2.1 ml of ethanolic potassium hydroxide (3M) with stirring at room temperature. After completed addition the solution was held at room temperature for two hours and then at 40° C for 16 hours. The reaction temperature was neutralised with hydrochloric acid (2M), further diluted with water and extracted with benzene. Washing with saturated sodium carbonate solution, drying ($Na_2SO_4$) and evaporation in vacuo gave an oily residue which was shown by TLC (silica, benzene as eluant) to contain at least four components. Column chromatography on silica (1 kg) with benzene as eluant gave the spiroketone XXVIII as colourless crystals, 2 g (31%) m.p. 113°–114° C.

d)

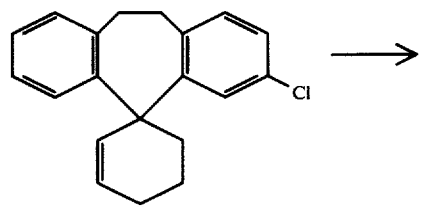

XXVIII

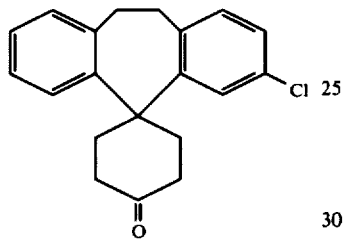

XXIX

The compound XXIX was prepared as described for compound XXIII. Yield 72%. m.p. 129°–131° from i-PrOH.

EXAMPLE 7.

Preparation of spiro[cyclohexane-1,5′(5′H)-dibenzo[a,d]cycloheptene]-4-one oxime

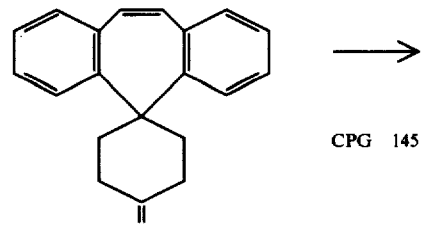

CPG 145

XXIII

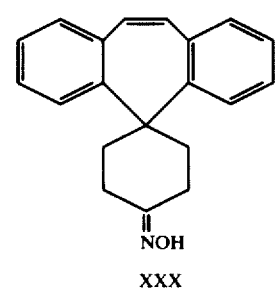

CPG 164

XXX 4 g of the ketone XXIII and 4 g of hydroxylamine hydrochloride in 40 ml of pyridine was heated under reflux for 2 hours. The mixture was then poured into 400 ml of water, the formed crystalline precipitate collected and washed with water. Recrystallization from acetonitrile gave 3.1 g (yield 73%) m.p. 181°–183° C.

EXAMPLE 8.

Preparation of 3-chlorospiro [5H-dibenzo [a,d] cycloheptene-5,1′-cyclohexane]4′one a)

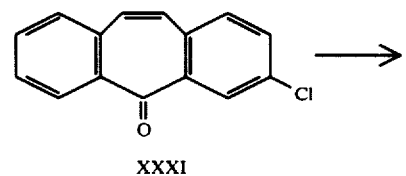

XXXI

[Structure]

SIR 108

XXXII

The compound XXXII was prepared as described for compound XVII but with methylal instead of THF as solvent. The starting ketone XXXI had poor solubility in dry methylal. It was added portionwise during 1 h. The yield was 82%. m.p. 92°–93° from EtOH.

b)

[Structure]

XXXII

[Structure]

SIR 110

XXXIII

The compound XXXIII was prepared as described for compound XVIII from the glycol ether XXXII in 51% yield. M.p. 133°–134° from i-$Pr_2O$.

c)

[Structure]

XXXIII

[Structure]

SIR 111

XXXIV

The compound XXXIV was prepared by the same procedure as described for compound XIX and isolated by column chromatography on Al₂O₃. Yield 41% m.p. 123°–125° from EtOH.

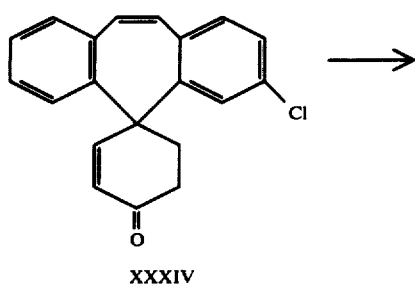

XXXIV

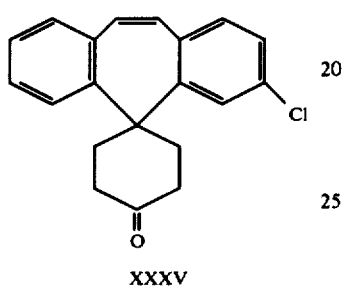

XXXV

The compound XXXV was prepared by the procedure described for compound XXIII. Yield 78% m.p. 132°–134° from i-PrOH.

EXAMPLE 9.

Preparation of methyl spiro[5H-dibenzo[a,d]cycloheptene-5,1'-cyclopentane]-3'-carbamate

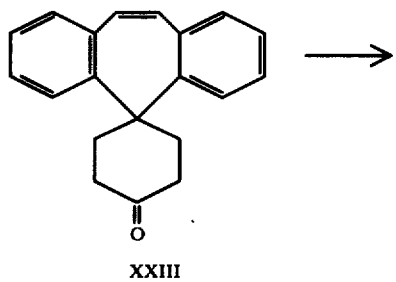

XXIII

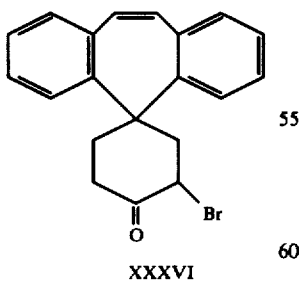

XXXVI

To a solution of 10.0 g (0.036 mole) of the cyclohexanone XXIII in 100 ml of CHCl₃ at 0°, was added dropwise 5.8 g (0.036 mole) of Br₂ (0.5 h). Then 100 ml of water was added, the organic phase separated, dried (Na₂SO₄) and evaporated. Trituration with 200 ml of Et₂O gave 7.7 g (60% m.p. 140°–142°.

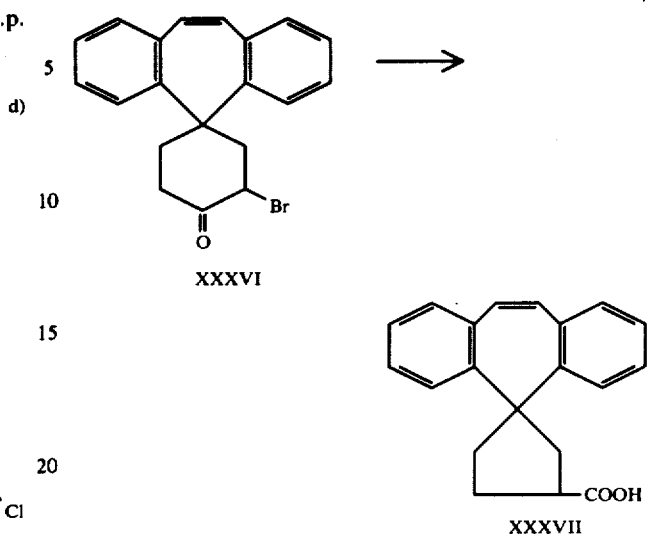

Portionwise addition of 4.6 g (0.013 mole) of the bromo ketone XXXVI to a stirred solution of NaOMe (made from 0.7 g (0.03 mole) in 50 ml of MeOH) at 0°, then at 20° for 5 h and evaporation gave equivalent yield of methyl spiro-[5H-dibenzo[a,d]cycloheptene-water (80 ml) and 10 N NaOH (2 ml) at 60° 1 for 2 hours. Et₂O was added, the aqueous phase washed with Et₂O and made acidic with diluted H₂SO₄. Extraction with 3×100 ml of Et₂O, drying (Na₂SO₄) and evaporation gave 3.7 g (97%), m.p. 110°–111° from n-hexane.

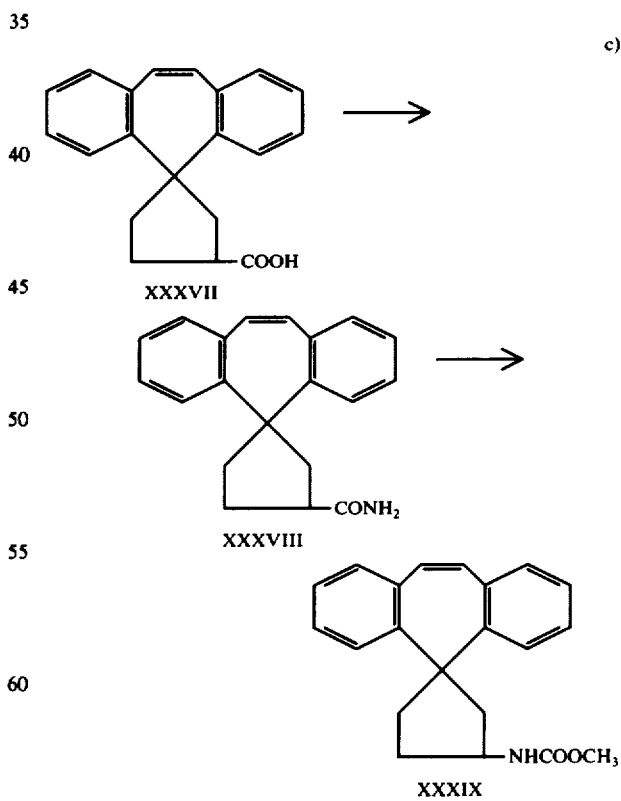

Treatment of 11.3 g (0,039 mole) of the acid XXXVII with 60 ml of SOCl₂ for 2 hours at reflux and evaporation gave a crude material of spiro[5H-dibenzo[a,d]cycloheptene-5,1'-cyclopentane]-3'-carboxylic acid chloride. To this was added 200 ml of Et₂O and the solution transferred to a dropping funnel. Gaseous NH₃ was bubbling through 150 ml of a mixture of Et₂O—C₆H₆ (1:1) with simultaneous adding of the acid chloride. The NH₃ inlet was continued for another 2 hours. Then water was added and the organic layer washed three times (H₂O). Drying (Na₂SO₄) and evaporation gave crystals upon trituration with boiling toluene. Total 7.4 g (65%) of spiro[5H-dibenzo[a,d]cycloheptene-5,1'-cyclopentane]-3'-carboxylamide XXXVII were collected. M.p. 181°-183°, NMR (CDCl₃) δ5.9 (b 2, CONH₂).

Then was added portionwise 6.5 g (0.023 mole) of 38 to NaOMe (made from 1.05 g (0.095 mole) of Na) in 150 ml of MeOH followed by 3.6 g (0.23 mole) of Br₂ at 0°. The solution was slowly heated to 50°. The excess MeOH was disposed of by evaporation and water was added. Extraction with CHCl₃ afforded crystals from Et₂O. Recrystallisation from Et₂O gave 5.8 g (81%) of XXXIX m.p. 65°-67°.

Preparation of end compounds

EXAMPLE 10.

Preparation of 4-(dimethylamino)spiro[2-cyclohexene-1,5'(5'H)dibenzo[a,d]cycloheptene]

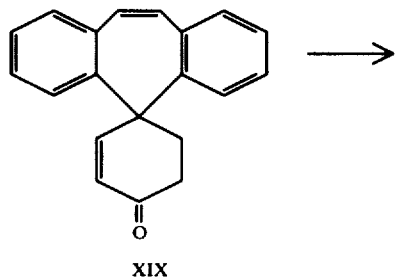

XIX

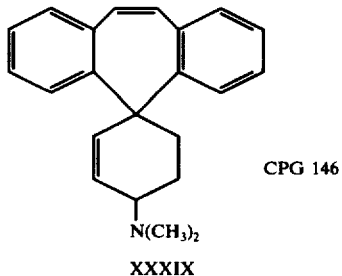

CPG 146

XXXIX

To 10 ml of liquid dimethylamine was added with care 2.0 g of formic acid (98%) at −15° C, and then a solution of 5.0 g of the spiroketone XIX (16.7 mmole) prepared according to example 1 in 12.5 ml of DMF. The mixture was heated under reflux for 5 hours, bath temperature 150° C. After dilution with ether the product was extracted with hydrochloric acid (2M). Alkalisation, extraction with ether, drying (Na₂SO₄), and evaporation gave 5 g of a colourless oil.

The picrate was prepared by mixing ether solutions of this oil and of picric acid giving 8 g of yellow crystals. Recrystallization from ethanol-acetone (25 ml + 50 ml) gave 5.7 g melting at 196°-203° C. The free amine XXXIX was secured by treating the picrate with sodium hydroxide solution (2M) and ether, drying and evaporation yielded 3.4 g of an oil (62%). Hydrochloride m.p. 185°-187° C.

EXAMPLE 11.

Preparation of 4-aminospiro[2-cyclohexene-1,5'(5'H) dibenzo[a,d]cycloheptene]

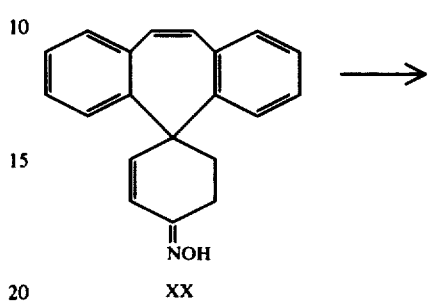

XX

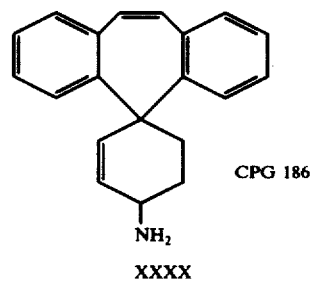

CPG 186

XXXX 6.5 g of the oxime (18 mmole) prepared according to example 2 dissolved in 250 ml of dry benzene was added with stirring at ambient temperature to 40 g of a benzene solution (70%) of sodium dihydro bis- (2 methoxyethoxy) aluminate. After refluxing the clear solution for four hours saturated aqueous sodium sulphate was added with cooling and the precipitated alumina filtered off. To the filtrate was added hydrogen chloride in diethyl ether (∼4 M) until the amine hydrochloride was completely precipitated. Stirring this hydrochloride with aqueous sodium hydroxide (2 M) and ether, drying the ether phase and evaporating gave the amine XXXX as an oil. 4.6 g, yield 88%. Maleate m.p. 188°-194° C.

EXAMPLE 12.

Preparation of 4-(methylamino)spiro[2-cyclohexene-1,5'-(5'H) dibenzo[a,d]cycloheptene]

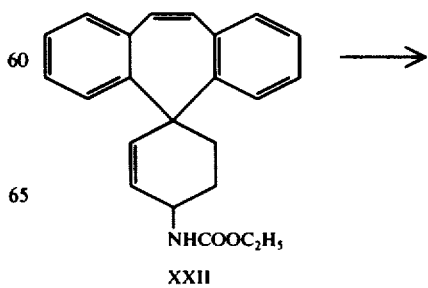

XXII

-continued

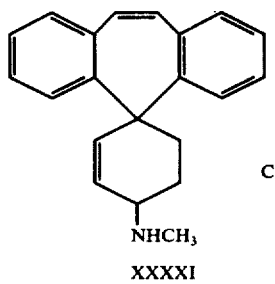

CPG 264

XXXXI 0.75 g of the urethane XXII (2.2 mmole) prepared according to example 3 dissolved in 50 ml of ether was added to a slurry of 0.25 g of lithium aluminium hydride (5.2 mmole) and the mixture heated under reflux for 5 hours. The hydride complex was destroyed by adding 5 ml of a saturated solution of sodium sulphate. To the filtered and dried solution was added hydrogen chloride in ether and the precipitated hydrochloride of the amine XXXXI was collected. Recrystallization from ethanol-water gave 0.5 g (71.5%) of colourless material m.p. 260° d. The hydrochloride is only sparingly soluble in water (181%).

EXAMPLE 13.

Preparation of
4-dimethylaminospiro[cyclohexane-1,5'(5'H)-dibenzo[-a,d]cycloheptene]

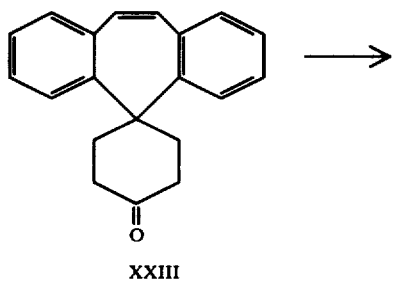

XXIII

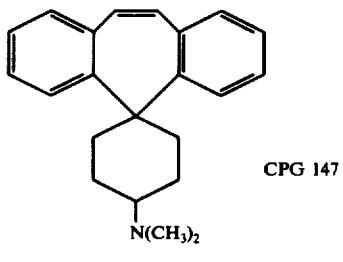

CPG 147

XXXXII

Using d3.4 g of the spiroketone prepared according to example 4, 4.2 g of dimethylamine and 1.2 g of formic acid in 7.7 g of DMF the reaction was performed as for compound XXX but with 4 hours heating and bath temperature 195° C. The extraction procedure gave 3.2 g of white colourless crystals of XXXXII melting about 90° C. Recrystallization from petroleum ether gave 1.9 g (68%) m.p. 101°–103°, further crystallization from ether gave an analytical sample m.p. 104°–105°. The hydrochloride, prepared from ethereal hydrogen chloride, melted at 180°–185° C.

EXAMPLE 14.

Preparation of
4-(methylamino)spiro[cyclohexane-1,5'(5'H)-dibenzo[-a,d]cycloheptene]

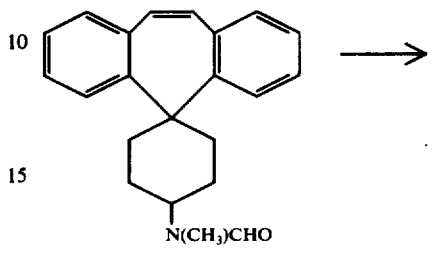

XXIV

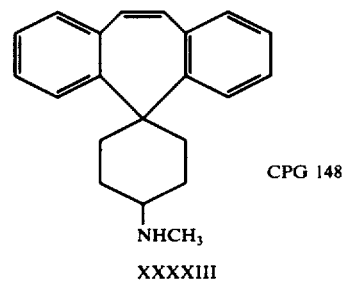

CPG 148

XXXXIII 1.5 g of the formyl compound XXIV prepared according to example 5 was dissolved in a mixture of 25 ml of dimethylsulfoxide and 5 ml of concentrated hydrochloric acid and heated at 100° C for three hours. Evaporation at reduced pressure gave a residue which was dissolved in 25 ml of water and washed with benzene. The solution was then made alkaline and extracted with benzene, which gave 1.2 g of an oil after drying and evaporation. 0.8 g of this oil in dry ether was mixed with an ether solution of malic acid to give a precipitate which was recrystallized from ethanol. 0.56 g of malate m.p. 194°–196° was obtained, and from the salt the amine XXXXIII was set free as an oil crystallizing on cooling and scraping. White crystals m.p. 85.5°–88°, yield 0.3 g, 33%.

EXAMPLE 15.

Preparation of 3'-chloro-10',
11'-dihydro-4-(dimethylamino)spiro[2-cyclohexene-1,5'(5'H)-dibenzo[a,d]cycloheptene]

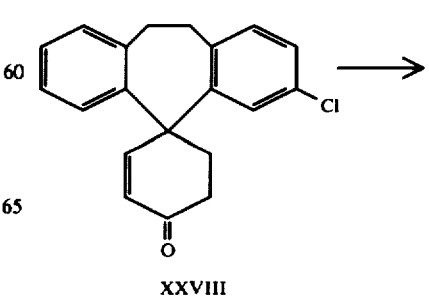

XXVIII

-continued

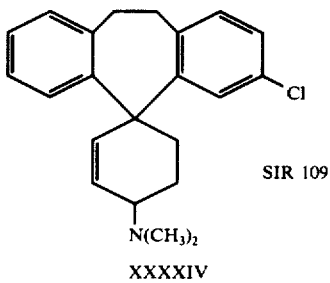

SIR 109

XXXXIV

A solution of 1 g of the ketone XXVIII prepared according to example 6 in 2 ml of DMF was added to dimethylammonium formate prepared from 0.25 ml of formic acid and 1.0 g of dimethylamin (confer prep. of compound XXX). The mixture was refluxed for 5 hours cooled, diluted with diethyl ether and extracted with hydrochloric acid (10%). The acid layer was alkalized and extracted with diethyl ether. Drying (Na$_2$SO$_4$) and evaporation gave a colourless oil which was again dissolved in dry diethyl ether and treated with hydrogen chloride (4-m in ether) to precipitate the hydrochloride of the amine XXXXIV (965 mg). Recrystallization from ethanol-ether gave 820 mg of crystals m.p. 241°-242° C.

EXAMPLE 15A.

Modified preparation of the tertiary amine XXXXIV, 3chloro-10′, 11′-dihydro-4-(dimethylamino)spiro [2-cyclohexene-1,5 (5′H)-dibenzo[a,d]cycloheptene]

When working on a larger scale it was found convenient to use the crude spiro ketone XXVIII (Ex. 6) without column chromatography. The crude ketone (250 g) was treated, as described in ex. 15, with dimethylammonium formate (from 80 ml of formic acid and 100 g of dimethylamine) in 500 ml of DMF. Amine work up gave an oil as in ex. 15. This crude amine weighed 155 g and was shown by gas-chromatography to contain about 80% of the amine. The hydrochloride was precipitated from ether and extracted with acetone. A residue of about 80 g was left and from the filtrate about 100 g of the free amine was isolated on alkalisation. It was further purified by column chromatography (3,5 kgSlO$_2$). Eluting with a mixture of methanol and acetone (3:7) gave 45 g of the amine. The hydrochloride melted at about 236° –43° (dec.) and gave a correct elemental analysis.

This preparation as well as the previous one from pure spiro ketone was analyzed by NMR spectroscopy and both were found to be a mixture of the two possible cis-trans isomers, here called α and β.

EXAMPLE 15B.

Separation of the cis-trans isomers of the amine XXXXIV 40 g of the amine XXXXIV was converted to its oxalate, which was recrystallized five times from acetonitrile. The last recrystallization caused no change in the NMR spectrum and the substance was therefore considered as a pure isomer, the β isomer. From the oxalate (12 g) the hydrochloride was prepared. M.p. 226°-8° (dec.). The mother liquors from the β-isomer were evaporated and the residue of amine oxalate was converted into the hydrochloride which was fractionally recrystallized from acetonitrile. Also here the separation was followed by NMR. The resulting α-isomer hydrochloride (10 g) had a m.p. 257°-9° C (dec.). The two isomers are clearly different in their NMR spectra, specially in the aromatic region, as shown below. The values given are δ-values in ppm from TMS as internal standard and with deuteriform as solvent.

| β-isomer | |
|---|---|
| Multiplet centered at | 7.0 |
| Multiplet centered at | 7.6 |
| (No peak at 7.10 as in α) | |
| α-isomer | |
| Multiplet with peak at | 7.10 |
| Quartet at | 7.55 |
| Doublet | 7.67 |

EXAMPLE 15C.

Resolution of the α-isomer of amine XXXXIV in its enantiomers

The amine salt with L(+)-mandelic acid was prepared from 10 g of the α-isomer hydrochloride. This salt was recrystallized four times from 2 -propanol. The resolution was followed by measuring the optical rotation. Finally the hydrochloride of the optically active amine was prepared, giving 2.5 with $[\alpha D_D^{20}] = 148$ ° (C = 0.8%, EtOH), m.p. 260°-1° (dec.). From the mother liquors the antipode was isolated, using D(-)-mandelic acid. The hydrochloride (3.2 g) showed $[\alpha]_D^{20} = -144°$ (c = b 0,5%, EtOH), m.p. 256°-8° (dec.).

EXAMPLE 16.

Preparation of 4-aminospiro [cyclohexane-1,5′ (5′H)-dibenzo[a,d]cycloheptene]

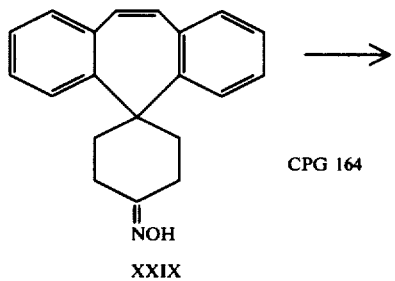

CPG 164

XXIX

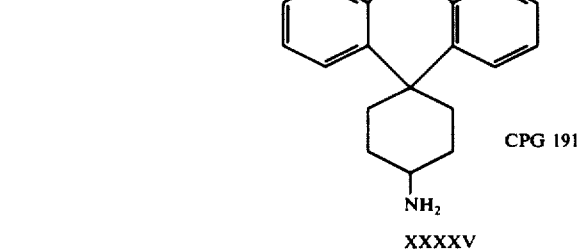

CPG 191

XXXXV 3 g of the oxime XXIX prepared according to Example 7, and 1,5 g of lithium aluminium hydride was refluxed in 300 ml of diethyl ether for 4 hours and then stirred at ambient temperature over night. The reaction mixture was worked up as described for XXXI. The amin XXXXV was isolated as its salt with maleic acid which was recrystallized from water. Yield 2 g (47 %) melting at 199°-200°

EXAMPLE 17.

Preparation of 3-chloro-10,11-dihydro-N,N-dimethylspiro[5H-dibenzo[a,d]cycloheptene-5,1'-cyclohexane]-4'-amine

XXIX

SIR 1

XXXXVI

Treatment of XXIX (2.0 g, 6.5 mmole) with dimethylammonium formate in DMF as described above for the preparation of XXXXII afforded 1.10 g (45 %) of the hydrochloride from i-PrOH. M.p. 270°–273°.

EXAMPLE 18.

Preparation of 3-chloro-N,N-dimethylspiro[5H-dibenzo[a,d]cycloheptene-5,1'-cyclohexane]-4'-amine

XXXV

SIR 118

XXXXVII

Treatment of XXXV (1.75 g, 5.7 mmole) with dimethylammonium formate in DMF as described above for the preparation of XXXXII gave 1.70 g (80 %) of the hydrochloride from EtOH—Et$_2$0 m.p.

Example 19.

Preparation of 3-chloro-N,N-dimethylspiro[5H-dibenzo[a,d]cycloheptene-5,1'-cyclohex-2'-ene]-4'-amine

XXXIV

SIR 114

XXXXVIII

Treatment of XXXIV (1.40 g, 4.6 mmole) with dimethylammonium formate in DMF as described above for the preparation of XXXXII gave 1.50 g crude product. The amine XXXXVIII was isolated by chromatography on basic alumina Woelm (160 g, activity and gradienteluted with C$_6$H$_6$- i-Pr$_2$O to give 1.20 g (77 %) of the desired amine. The hydrochloride from EtOH had m.p. 232°–235° C.

EXAMPLE 20. Preparation of spiro[5H-dibenzo[a,d]cycloheptene-5,1'-cyclopentane]-4'-amine

XXXVII

XXXXIX

To 11 g (0.038 mole) of acid XXXVII in H$_2$O (6 ml) and Me$_2$CO (50 ml) at 5° was added 4.6 g (0.045 mole) of triethylamine in Me$_2$CO (50 ml). Then 5.4 g (0.049 mole) of ethyl chloroformate in Me$_2$CO (20 ml) was slowly added and the mixture was stirred at 10° for 2 hours. Cooling to 0°, addition of 3.7 g (0.057 mole) of NaN₃ in H₂O (15 ml) and then stirring at 10° for another 2 hours, pouring the mixture into 500 ml of cold water, gave an oil which was taken up in Et₂O. The etheral phase was reduced to 50 ml and added to 100 ml of 70 % AcOH (aq), and heated at 100 ° for 2 hours, addition of 100 ml of concentrated HCl and then standing at 100° over night gave 3.0 g (26 %) of desired product after extraction of the alkaline made solution with Et₂O and distillation, b.p. 180°/0.1 mm Hg. Hydrochloride Pharmaceutical preparations m.p. 145°–147° C

EXAMPLE 21.

Preparation of tablets

Each tablet contains:

| | |
|---|---|
| 3'-cloro-10', 11'-dihydro-4-(di-methylamino)spiro [2-cyclohexene-1,5'(5'H)-dibenzo[a,d]cycloheptene] | 10 mg |
| Lactose | 60 mg |
| Starch | 29 mg |
| Magnesium stearate | 1 mg |

The powders are mixed and directly compressed to tablets with a diameter of 6 mm.

The active substance shown above may be replaced by other pharmaceutically acceptable acid addition salts according to the invention.

EXAMPLE 22.

Preparation of tablets

| | |
|---|---|
| 3'-chloro-10',11'-dihydro-4-(di-methylamino)spiro [2-cyclohexene-1,5'(5'H)-dibenzo[a,d]cycloheptene] | 50 mg |
| Aerosil ® (silicium dioxide) | 20 mg |
| Lactose | 100 mg |
| Starch | 30 mg |
| Magnesium stearate | 2 mg |

The active principle is mixed with the Aerosil ®. This mixture is added to the other powders. Tablets are compressed with a diameter of 10 mm.

The active substance shown above may be replaced by other pharmaceutically acceptable acid addition salts according to the invention.

EXAMPLE 23.

Preparation of capsules

| | |
|---|---|
| 3'-chloro-10', 11'-dihydro-4-(di-methylamino)spiro [2-cyclohexene-1,5'(5'H)-dibenzo[a,d]cycloheptene] | 20 mg |
| Peanut oil | 60 mg |

The solution is filled into soft gelatine capsules. Each capsule containing 20 mg of the active principle.

The active substance shown may be replaced by other pharmaceutically acceptable acid addition salts according to the invention.

EXAMPLE 24.

Preparation of capsules

| | |
|---|---|
| 3'-chloro-10', 11'-dihydro-4-(di-methylamino)spiro- [2-cyclohexene-1,5'(5'H)-dibenzo[a,d]cycloheptene] | 10 mg |
| Polyoxyethylene sorbitane monoleat | 100 mg |

The capsules are made as described in Example 17.

The active substance shown above may be replaced by other pharmaceutically acceptable acid addition salts according to the invention.

PHARMACOLOGICAL METHODS

A. Biochemical tests

1. Inhibition of the uptake of tritiated 5-HT in vitro and in vivo

The method is described by Ross and Renyi in European Journal of Pharmacology 7 (1969), 270–277. Tricyclic antidepressant drugs of type imipramine given in vivo to mice decrease the uptake of ³H-5-HT in vitro. The drugs were administered intraperitoneally half an hour before the animals were killed and the midbrain was taken out and sliced and incubated in a mixture consisting of, per 100 mg of brain slices, 0.2 $\mu$mole of ³H-5-HT and 1 $\mu$mole of glucose in 2 ml of Krebs-Henseleit buffer, pH 7.4. The incubation time was 5 minutes with 5 minutes of preincubation before ³H-5-HT was added. The radioactive ³H-5-HT taken up in the slices was extracted with ethanol and the amount was determined by liquid scintillation. The dose producing 50 per cent decrease of the active uptake ($ED_{50}$) was determined graphically from dose response curves. Active uptake is defined as that part of the radioactive uptake which is inhibited by a high concentration of cocaine. All doses were given at least to four animals.

2. Inhibition of the uptake of tritiated noradrenaline in vitro and in vivo

The method is found in European Journal of Pharmacology 2 (1967), 181–186. The animals were killed half or one hour after the administration of the drugs in vivo (i.p.). The slices, made from cortex, were preincubated for five minutes and incubated with 0.1 $\mu$mole per ml of ³H-noradrenaline for further five minutes. The incubation mixture consisted of 0.2 $\mu$mole of ³H-NA and the brain slices in 2 ml of Krebs-Henseleits buffer, pH 7.4. The radioactive ³H-NA taken up in the slices was extracted with ethanol and the amount was determined by liquid scintillation. The dose producing 50 per cent decrease of the active uptake ($ED_{50}$) was determined graphically from dose response curves. At least four animals were used at each dose level.

B. Pharmacological tests 1. 5-HTP response potentiation test

Inhibition of the uptake of 5-HT potentiates the effects of administered 5-hydroxytryptophan (5-HTP probably by increasing the amount of 5HT at the receptor. Three mice are given the test drugs one hour (or 4, 24 hours) before dl-5-HTP 90 mg/kg i.v. 5-HTP alone gives only a weak behavioural syndrome but in pretreated mice there is seen a characteristic behavioural syndrome, which comes within 5 minutes: tremor, lordosis, abduction of the hindlegs, head-twitches.

These small movements are quantitatively measured in an activity box, type Animex, which can distinguish between small and gross movements. The activity is measured during 20 minutes and only in the case the animals have a fullblown syndrome. Each group consists of 3 animals and at least 4 groups were tested at 25 mg/kg i.p. Control groups receiving imipramine (Tofranil ®) are used as reference, since imipramine constantly potentiated dl-5-HTP.

2. Dopa response potentiation test control values 10 minutes after injection. $PD_{200}$ is the dose which increases the pupill by 200%.

| Substance | Inhibition (50 %) of uptake | | | | Potentiation of | | Motor acti- vity $ID_{50}$ | Peripheral anti-cholinergic action $PD_{200}$ mg/kg i.v. | Acute toxicity $LD_{50}$ mg/kg i.v. | Arrythmia (rabbit) Accumulated i.v. dose where there are signs of arrythmia |
|---|---|---|---|---|---|---|---|---|---|---|
| | in vitro | | in vivo | | 5-HTP[3] | 1-Dopa[4] | | | | |
| | 5-HT[1] | NA[2] | 5-HT[1] | NA[2] | Effective dose, | | | | | |
| | µg/ml | | mg/kg i.p. | | mg/kg i.p. | | | | | |
| CPG 186 | >10 | 1.5 | 28 | 14 | 25 | >10 | >50 | >25 | 25 | M >10 |
| CPG 264 | 1.3 | 0.3 | >40 | 1.3 | >25 | >10 | 13 | 2.5 | 25 | — |
| CPG 146 | 4 | 0.02 | >40 | 1.7 | — | — | — | 1 | 30 | — |
| SIR 109 | 1.3 | 1.5 | >40 | 40 | —[5] | —[5] | 5 | — | — | — |
| CPG 147 | 4 | 0.05 | >40 | 1.5 | >25 | 2.5 | 27 | 1 | 32 | — |
| CPG 191 | 2 | 1.5 | >40 | >40 | >25 | >10 | 53 | <10 | 32 | |
| CPG 148 | 3 | 1.5 | >40 | >40 | >25 | >10 | 35 | 3.5 | 60 | |
| SIR 117 | 5 | 1.5 | >40 | >40 | >25 | >10 | 14 | 15 | 27 | |
| SIR 118 | 4 | 1.5 | >40 | >40 | >25 | >10 | 11 | 9 | 18 | |
| SIR 114 | 7 | 2.5 | >40 | >40 | >25 | >10 | 5.5 | 15 | 22 | |
| Imipramine | 0.1 | 0.06 | 24 | 6 | 25 | 10 | 45 | 13 | 28 | |

[1]5-HT = 5-hydroxytryptamine
[2]NA = dl-noradrenaline $10^{-7}M$
[3]5-HTP = 1-5-hydroxytryptophan
[4]l-DOPA = 1-3,4-dihydroxyphenyl-alanine
[5]impossible to test because tranquilizing effect of the compound.

Inhibition of monoamine oxidase together with blockage of the uptake of NA potentiate the effects of administrated l-Dopa. This test is developed by G.M. Everett (Antidepressant drugs,ed. S. Carattini, 1966).

Mice in groups of 3 are pretreated with Pargyline ®40 l mg/kg p.o. about 10–16 hours before the test. The test drugs are given i.p. one of four hours before l-Dopa 100 mg/kg i.p. The mice are observed for one hour after l-Dopa administration. l-Dopa gives a characteristic syndrome which is scored as follows:

1. piloerection, slight salivation, slight increased motor activity
2. piloerection, salivation, marked increased motor activity and irritability
3. piloerection, profuse salivation, marked irritability and reactivity, jumping, squeaking, fighting.

The control groups are Amitriptyline (20 mg/kg i.p. 4 hours before l-Dopa) and saline (1 hour before l-Dopa). Amitriptyline always scores three at this dose whereas saline gives a one score. The test drugs were all tested at 10 mg/kg i.p.

Motor activity in mice

The exploratory activity of mice was recorded in a locomotion cage in which the movements were counted each time the animals cross-circuits on electrical current in the bottom plate. The activity was recorded for ten minutes one hour after the administration of the drug. The animals were tested individually. Groups of six mice were used and the mice were only used once. The activity was expressed in percent of the activity of control groups ran simultaneously.

Drug induced arrhytmias in rabbits

Test drugs were intravenously administered to male rabbits anesthesized wth amytal. The doses were increased stepwise up to the lethal dose and the first dose which induced arrhythmia was noted.

Acute toxicity, behaviour and anticholinergic study in mice

The compounds were given by intravenous route to 3 mice. $LD_{50}$ is the dose which kills 50% of the animals within 24 hours. Seizures, gait, sedation and grip strength were recorded. Pupil width (mydriasis) which reveals peripheral anticholinergic action was measured in green light. These data are expressed in percent of

EVALUATION OF THE RESULTS OBTAINED IN THE PHARMACOLOGICAL TESTS

The results are summarized in the table. The compounds of the invention block both the uptake of noradrenaline and 5-hydroxytryptamine in brain slices in vitro and in vivo. Three compounds CPG 146, 147 and 264 are about three times as effective as imipramine in blocking the uptake of noradrenaline in vivo, whereas CPG 186 blocks the uptake of 5-HT in equivalent doses. The interactions with 5-hydroxytryptophan and l-dopa correlates well with the uptake inhibition of noradrenaline and 5-hydroxytryptamine. The intravenous toxicity of the compounds is about comparable to that of imipramine. CPG 186 is devoid of the anticholinergic effects shared by imipramine and the other compounds presented in the table and CPG 186 did not cause arrhythmia in nonlethal doses in rabbits which imipramine did and gave sedation only in high doses. Some of the compounds were strongly sedative or tranquilizing such as SIR 109.

The results indicate that in this series of compounds it is possible to differentiate the uptake inhibition from the unwanted side effects and to find potent and selective inhibitions of the amine uptake in the brain.

FURTHER PHARMACOLOGICAL TESTS

Most of the pharmacological tests below have been performed with the isomer mixtures prepared as described in ex. 15. Tests on the separated α and β-isomers respectively show that the biological activity mainly originates from the β-isomer at least for "conditioned avoidance response" (CAR).

METHODS

Introduction

At present there are no single tests, which will clearly and reliably indicate the existence of a neuroleptic action. A battery of biochemical and behavioral tests have been developed based on consensus of opinion and taken together they fulfil the biochemical and behavioral criteria for neuroleptic action. These criteria are: blockade of conditioned responses, inhibition of amphetamine hyperactivity and inhibition of Dopamine receptors in the brain. (1,2,3) The relations of these effects to the toxicological and particularly the cataleptic properties determine the potential value of a compound as a neuroleptic agent, since drug induced parkinsonism is one of the main disadvantages with prior art compounds. Other properties such as anxiolytic and sedative effects are interesting and important aspects of the pharmacological profile.

Material

The drugs were dissolved immediately before use in 0.9% sodium chloride solution or suspended in 1% Methocel. The doses were administered to the mice in a volume of 0.20 ml/20 g body weight. All control groups were given the corresponding volume of 0.9% sodium chloride solution. The experiments were performed in localities at a constant temperature U+20° C) and constant humidity (40–50%). The following compounds were tested: chlorpromazine hydrochloride (CPZ), SIR 109 (cis-trans racemate), SIR 114, SIR 117, SIR 118, SIR 124 ($\alpha$-isomer of SIR 109), SIR 125 ($\beta$-isomer of SIR 109).

Subjects

The experiments were performed on male mice and male rats. The animals had free access to food and water before the experiments and during long term experiments. They were used only once.

Estimation of DA and NA receptor blockade in the rat brain

The estimation of catecholamine (CA) turnover was made by using the tyrosine hydroxylase inhibitor $\alpha$-methyl tyrosine methyl ester (H 44/68) (4). This technique is based on the assumption that dopamine (DA) or noradrenaline (NA) receptor blockade will mediate an increase in CA turnover and result in lowered CA levels in the brain compared to H 44/68 alone. Since DA receptor blockade is assumed to be a biochemical correlate to antipsychotic action, this test gives a biochemical evidence for an antipsychotic effect. In this particular test the DA and NA levels in the brain were measured biochemically (5,6).

Conditioned avoidance response in rats

Chlorpromazine and other neuroleptics inhibit many different types of learned responses. For this reason the conditioned avoidance test has been developed for initial screening of neuroleptics. Rats were trained to avoid electrical shock by jumping from one compartment to the other in a shuttle box. The conditioned stimulus consists of an auditory signal which after eight seconds was followed by the electrical shock. The rates were trained to a criterion of making eight out of ten responses correctly. The drugs were injected one hour before the test. The avoidance responses are expressed in percentage of those before administration. $CD_{50}$ is the dose which reduces the avoidance response to 50% of control values.

Antagonism of methamphetamine-induced hyperactivity

It has been found that neuroleptics (e.g. phenothiazines, butyrophenones) in higher doses block and in very small doses potentiate hyperactivity induced by amphetamines. Sedatives (e.g. barbiturates, benzodiazepines and propandiols) on the other hand generally potentiate the induced hyperactivity. The interaction with amphetamines consequently gives an indication of the mechanism of a drug. Male mice were pretreated with the test drug 30 minutes before the administration of methamphetamine 3 mg/kg i.p. After 20 minutes the spontaneous motor activity was measured for 20 minutes by an Animex activity meter, which can distinguish between slight and considerable motion. The animals were tested in groups of three and used only once. Control groups treated with saline alone or the test drug and saline according to the testing schedule were run simultaneously.

Catalepsy

Using the method and intensity scaring system described by Costall and Naylar, (7), the cataleptic properties of SIR 109 and chloropromazine were studied. Briefly, an animal was classed as cataleptic if it remained in an abnormal position for 15 seconds. Additionally, the duration the animal held this position was converted to a numerical scare as an indication of the intensity of the catalepsy.

Motor activity

Sedative activity was defined as suppression of normal motor activity. The motor activity in mice was automatically recorded in a locomotion cage in which the movements are counted each time the animal short-circuits an electrical current in the bottom plate. The activity was recorded for 10 minutes one hour after the administration of the drug. The animals were tested individually. Groups of six mice were used. The activity was expressed in percent of the activity of control groups run simultaneously. $ED_{50}$ is the dose which reduces the activity to 50% of the activity of the control groups and was computed from the log dose-response curve.

Aggressive behavior

Anxiolytic effect was defined as a block of aggressive behavior in mice. Male mice kept isolated for 3 weeks or longer develop an aggressive behaviour when caged together. The method used followed that reported by Valzelli et al. (8) with the exception that two mice were tested together. The aggressiveness was scored during a five minute test according to the following scale:
- 0: the animals show no interest in each other except occasional nosing,
- 24: frequent vigorous nosing and tail twitching. The animals assume a fighting position and occasionally attack the partner — no more than 3–4 times in the period of five minutes,
- 50: tail twitching, powerful attacks — no more than 10 times during the test period,
- 75: the animals pursue their partners, attacking and biting for most of the time,
- 100: attacks over the entire period.

Controls administered with the solvent were tested. The repeated testing did not influence the aggressive behaviour. The animals were used for several experiments but with intervals of at least one week. Groups of 10 mice were used, and they were tested one hour after the administration of the drug. The animals were used as their own controls. Inhibitory dose ($ID_{50}$) reduces the aggression score to 50% of its pretreatment value.

Toxicity, behavioral observation and peripheral parasympatholytic effect

Acute toxicity was tested by the intraveneous, intraperitoneal and oral routes of administration. The animals were observed for 24 hours. During the oral route a behavioral scoring system was used in order to relate changes in behavior to dose. The $LD_{50}$ values were determined graphically from log dose — response curves based on four doses with three animals per dose. Peripheral parasympatholytic effect was tested in mice by observing the mydriatic effect after intravenous injection (9) (four doses with three animals per dose). $PD_{200}$ refers to the dose which increases the pupil width by 200%.

RESULTS. EFFECTS ON DA AND NA TURNOVER

Both SIR 109 and chlorpromazine (CPZ) effects DA turnover at about the same dose (Table 2). SIR 109 seems to be more selective than chlorpromazine since it influences NA turnover first at higher doses.

EFFECTS ON CONDITIONED AVOIDANCE RESPONSE AND CATALEPSY IN THE RAT

See Table 3. SIR 109 is somewhat less active than chlorpromazine. Interestingly enough one of the isomers SIR 125 (β-isomer) is more potent than the racemate SIR 109 and also more potent than CPZ. The α-isomer, SIR 124, on the other hand seems to have a relatively weak effect on CAR. SIR 109 has a weak cataleptic effect in the rat compound to CPZ (table 3). Also the intensity of catalepsy was considerably lower after SIR 109 compared to CPZ.

EFFECTS ON MOTOR ACTIVITY (TABLE 4) AND ANTIAMPHETAMINE EFFECTS

SIR 109 and SIR 114 caused sedation in the mice at about the same dose as CPZ. The other SIR compounds SIR 117 and SIR 118 were somewhat less active.

Both SIR 109 and CPZ blocked methamphetamine induced hyperactivity in mice (FIG. 1).

EFFECTS ON AGGRESSIVE BEHAVIOR IN MICE

SIR 109 was potent at a dose which does not cause sedation (TABLE 4). CPZ was effective first at sedative doses.

TOXICITY, BEHAVIORAL OBSERVATION AND PERIPHERAL PARASYMPATHOLYTIC EFFECTS

SIR 109 is considerably less toxic than CPZ both after i.v., i.p. and oral administration in the mice. (Table 4). SIR 109 was also weak peripheral effects. The other SIR compounds, SIR 114, 117 and 118 have an intravenous toxicity in the same range as CPZ.

Behavioral observation showed that SIR 109 in contrast to CPZ caused ptosis first at high doses. Threshold dose for SIR 109 was 31 mg/kg and for CPZ 4 mg/kg. Furthermore, SIR 109 did not cause any catatonic state which was prominent after CPZ from 31 mg/kg orally in the mice.

CONCLUSION

It is concluded that SIR 109 and its isomers and analogues all fulfill the criteria for neuroleptic action. SIR 109 is about as potent as chlorpromazine in affecting DA turnover and conditioned avoidance response and in blocking motor activity and methamphetamine hyperactivity. However, SIR 109 is a more selective compound than chlorpromazine since it affects NA turnover first at higher doses. The strong effect of SIR 109 on aggressive behavior at non-sedative doses could indicate that SIR 109 in contrast to CPZ has pronounced anxiolytic properties. Furthermore, SIR 109 has low cataleptic action and causes ptosis first at high doses. Compared to chlorpromazine, SIR 109 is considerably less toxic after acute administration. The possibility of obtaining a more potent and selective compound is obvious since SIR 125, the β-isomer, is more potent than both SIR 109 and chlorpromazine.

SIR 109 and its isomers therefore could fulfill the old wish of obtaining a compound with strong neuroleptic action combined with few peripheral and central side effects, such as ptosis and drug induced parkinsonism.

The strong anxiolytic action of SIR 109 could in this context be an interesting asset.

Table 2

| Effects of SIR 109 and chlorpromazine on brain catecholamine levels in the rat after tyrosine hydroxylase inhibition by H 44/68, 250 mg/kg i.p. The first significant dose was estimated | | |
|---|---|---|
| | Dopamine | Noradrenaline |
| SIR 109 | 5 mg/kg i.p. | 10 – 15 mg/kg i.p. |
| Chlorpromazine | 5 mg/kg i.p. | 5 mg/kg i.p. |

Table 3

Effects of SIR 109 and its isomers on conditioned avoidance response (CAR) and catalepsy in one rat.

| | CAR | Catalepsy | |
|---|---|---|---|
| | $CD_{50}$ mg/kg i.p. | $ED_{50}$ mg/kg i.p. | Intensity score |
| SIR 109 | 7.5 – 10 | 25 | 0.75 |
| SIR 124 α | >10 | — | — |
| SIR 125 β | <2.5 | — | — |
| Chlorpromazine (CPZ) | 5 | 7 | 1.0 |

Table 4

| Code | Structure | Motor activity $ID_{50}$ mg/kg i.p. | CAR $ED_{50}$ mg/kg i.p. | Anti-aggresive test $ED_{50}$ mg/kg i.p. | $LD_{50}$ mg/kg i.v. | $LD_{50}$ mg/kg i.p. | $LD_{50}$ mg/kg p.o. | $PD_{200}$ mg/kg i.v. |
|---|---|---|---|---|---|---|---|---|
| SIR 109 | 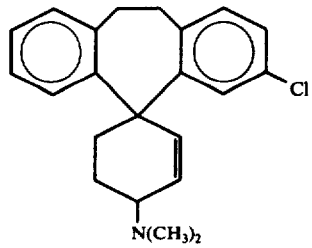 | 5 | 7.5 – 10 | 0.27 | 40 | 185 | 250 | >40 |

Table 4-continued

| Code | Structure | Motor activity ID$_{50}$ mg/kg i.p. | CAR ED$_{50}$ mg/kg i.p. | Anti-aggresive test ED$_{50}$ mg/kg i.p. | LD$_{50}$ mg/kg i.v. | LD$_{50}$ mg/kg i.p. | LD$_{50}$ mg/kg p.o. | PD$_{200}$ mg/kg i.v. |
|---|---|---|---|---|---|---|---|---|
| SIR 114 | 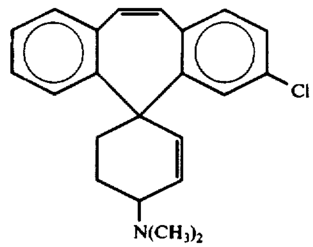 | 5.5 | | | 22 | 130 | | 15 |
| SIR 117 | 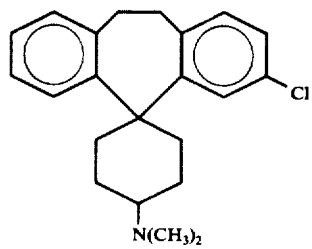 | 14 | | | 27 | | | 15 |
| SIR 118 | 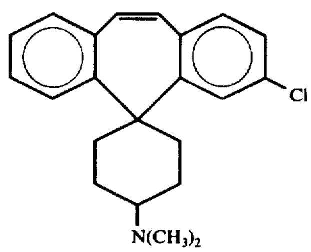 | 11 | | | 18 | | | g |
| Chloropromazine | 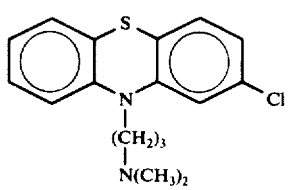 | 5 | 2 | | 26 | 92 | 190 | |

REFERENCES

1. A. Carlsson and M. Lindqvist, Acta Pharmacol, Toxicol. 20, 140, 1963.
2. J. W. Kebabiau, G. L. Petzold, P. Greengard, Proc. Natl. Acad. Sci. USA, 69, 2145, 1972.
3. A. Randrup in Modern problems of Pharmacopsychiatry vol. 5, (S. Karger, Basel, 1970), p. 60.
4. N. E. Anden, H. Corrodi and K. Fuxe, in Metabolism of amines in the brain, (MacMillan, London, 1969), P. 38.
5. A. Butler, A. Carlsson, and E. Rosengren, Acta Physiol, Scand., 44, 273, 1958.
6. A. Carlsson and B. Waldecy, Acta Physiol, Scand, 44, 293, 1958.
7. B. Costall and R. J. Naylar, Azneim. - Forsch., 23, 674, 1973.
8. L. Valzelli, E. Giacalone and S. Garattini, Eur. J. Pharmacol., 2, 144, 1967.
9. R. A. Turner in Screening Methods in Pharmacology, Academic Press, New York, N.Y., 1965, p. 174.

What we claim is:

1. A compound selected from the group consisting of

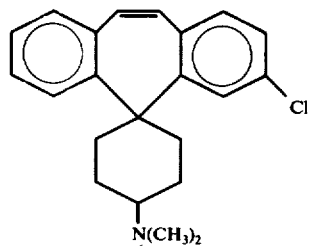

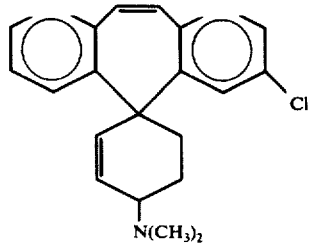

-continued

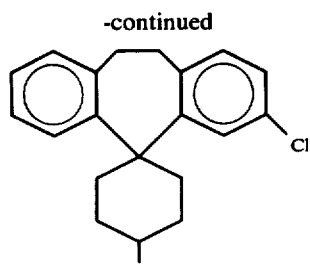

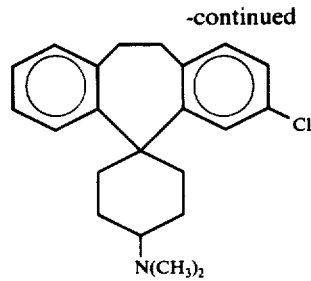  IX

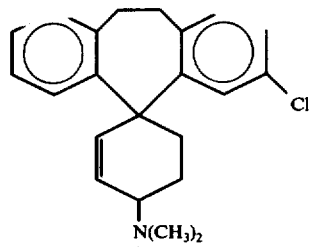

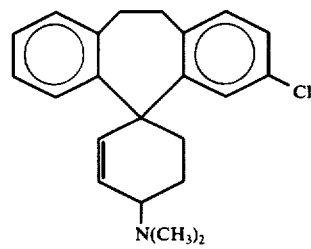  X and pharmaceutically acceptable salts thereof.

2. A compound according to claim 1 in the form of a pure cis or trans isomer, whenever such an isomer is possible.

3. A compound according to claim 1 in the form of an optically pure isomer.

4. A method of treatment of psycotic conditions of different origins in man characterized in the administration of a therapeutically effective amount of a compound of claim 1 or a therapeutically acceptable acid addition salt thereof.

5. A method of treatment of neurotic conditions of different origins in man characterized in the administration of a therapeutically effective amount of a compound of claim 1 or a therapeutically acceptable acid addition salt thereof.

6. A pharmaceutical preparation for the treatment of psychotic or neurotic conditions of different origins in man, containing as active ingredient a compound of the group consisting of compounds having the formula in combination with a pharmaceutically acceptable carrier, the amount of said active ingredient being about 0.1 to 95% by weight of the preparation.

7. A pharmaceutical preparation according to claim 6, containing as active ingredient the compound 3'-chloro-10',11'-dihydro-4-(di-methylamino)spiro[2-cyclohexene-1,5'(5'H)-dibenzo[a,d]cycloheptene] in combination with a pharmaceutically acceptable carrier.

8. A pharmaceutical preparation for the treatment of psychotic or neurotic conditions of different origins in man, containing as active ingredient a compound of a group consisting of compounds having the formula

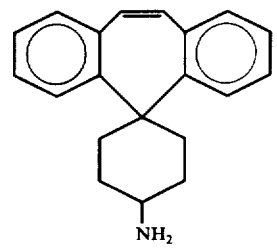  I

VII

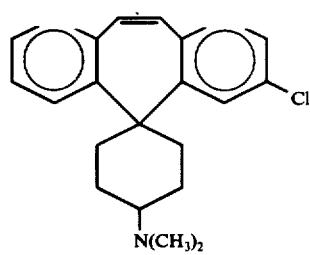

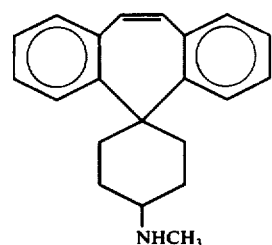  II

VIII

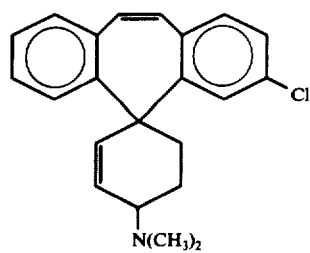

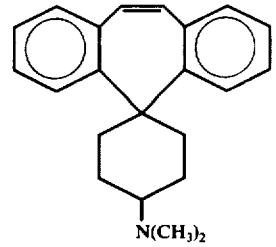  III

-continued

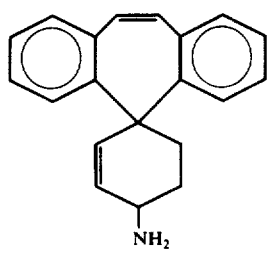
IV

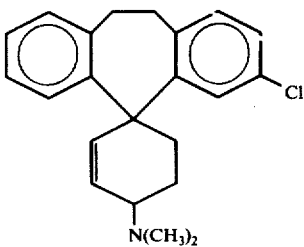
X

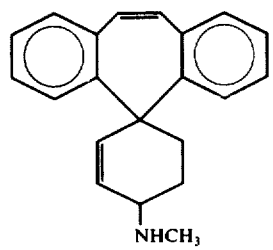
V

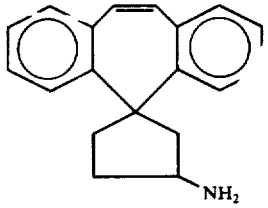
XI

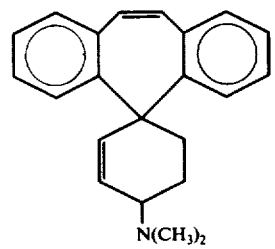
VI in combination with a pharmaceutically acceptable carrier, the amount of said active ingredient being about 0.1 to 95% of the preparation.

9. A pharmaceutical preparation as described in claim 8 intended for injection and containing from 0.5 to 20% by weight of the active ingredient.

10. A pharmaceutical preparation as described in claim 8 intended for oral administration and containing from 2 to 50% by weight of the active ingredient.

11. A compound of the formula

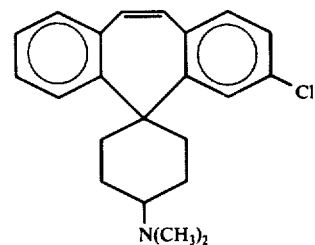
VII

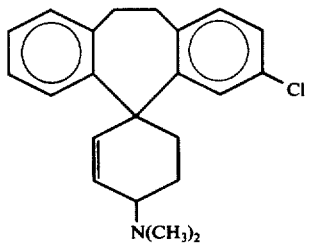

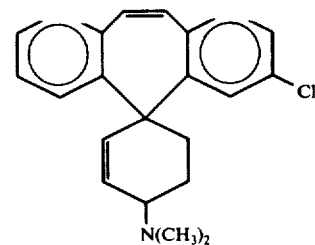
VIII in the form of the cis-trans isomer of the cis-trans isomer pair, which cis-trans isomer has the lowest melting point as racemate hydrochloride, and which has a NMR spectrum with a multiplet centered at 7.0 and no peak at 7.10, the NMR values given being δ-values in ppm from TMS as internal standard with deuterioform as solvent.

12. A compound according to claim 11 in the form of an optically pure isomer.

13. A pharmaceutical preparation for the treatment of neurotic conditions or psychotic conditions of different origins in man containing as active ingredient a compound according to claim 1 in combination with a pharmaceutically acceptable carrier, the amount of said active ingredient in said preparation being from 0.1 to 95% active ingredient in said preparation being from 0.1 to 95% by weight of said preparation.

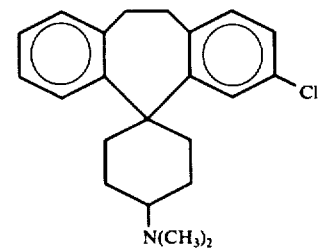
IX

14. A method for the treatment of psychotic conditions of different origins in man comprising the administration to a person suffering from said condition of a therapeutically effective amount for the relief of psychosis of a compound having the formula -continued
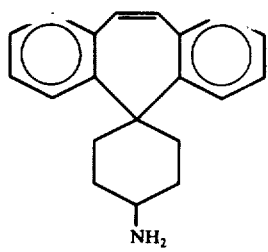
I
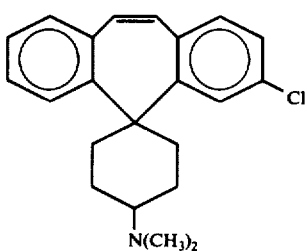
VII
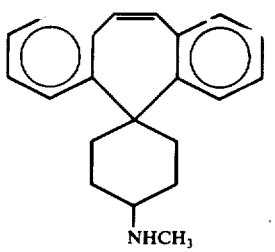
II
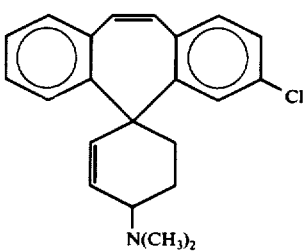
VIII
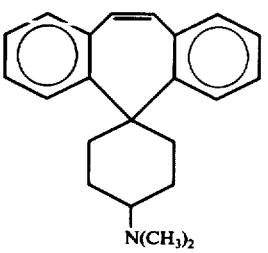
III
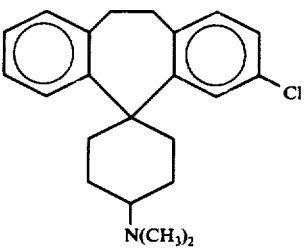
IX
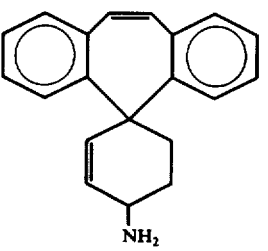
IV
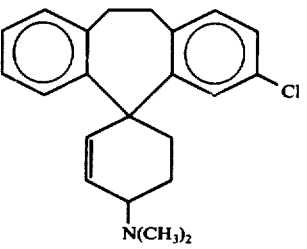
X
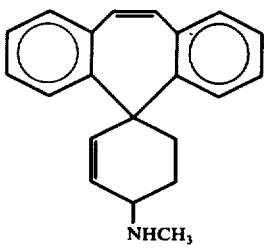
or
V
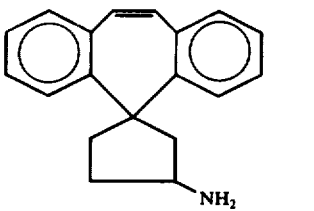
XI
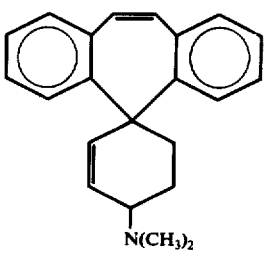
VI
or a therapeutically acceptable acid addition salt thereof.
15. A method for the treatment of neurotic conditions of different origins in man comprising administering to a person suffering from such condition of a therapeutically effective amount for the relief of neurosis of a compound having the formula -continued
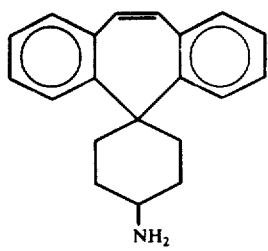
I
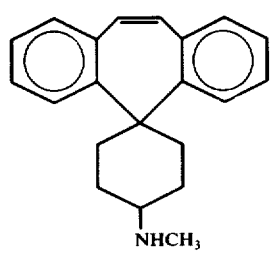
II
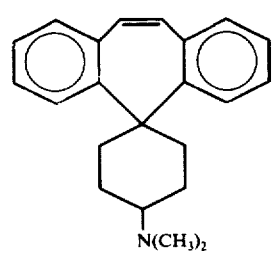
III
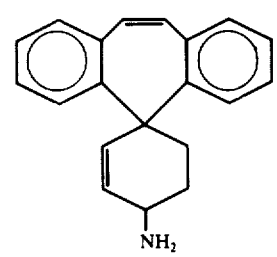
IV
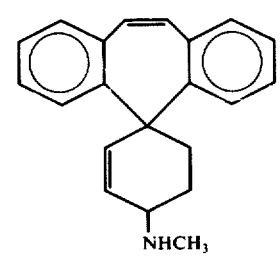
V
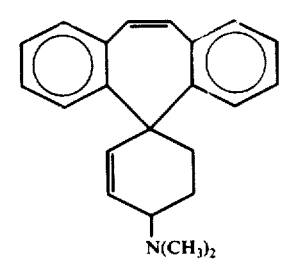
VI
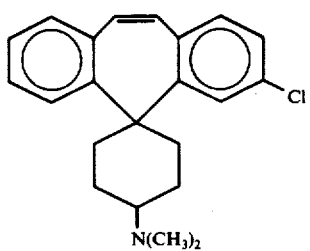
VII
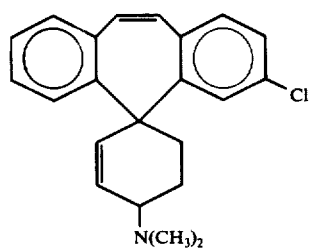
VIII
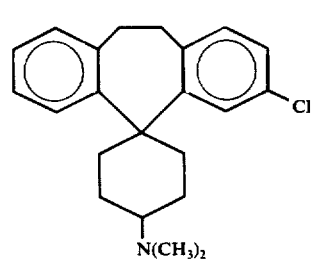
IX
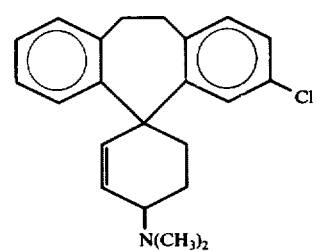
X
or
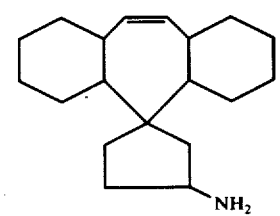
XI
or a therapeutically acceptable acid addition salt thereof.
16. A method for the treatment of psychotic conditions of different origins in man comprising administering to a person suffering from such condition of a therapeutically effective amount for the relief of psychosis of a compound having the formula -continued

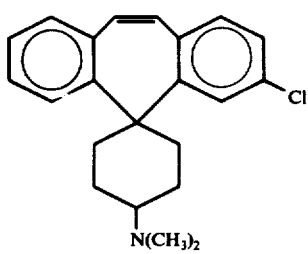

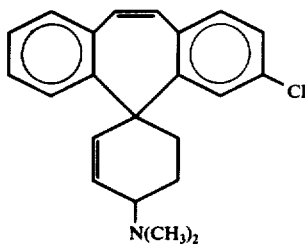

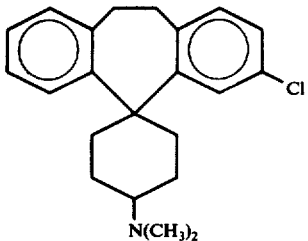

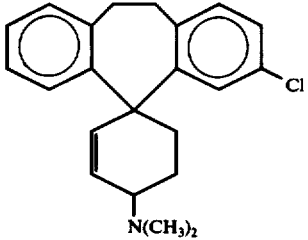

or a therapeutically acceptable acid addition salt thereof.

17. The method as described in claim 16 wherein compound administered has the formula

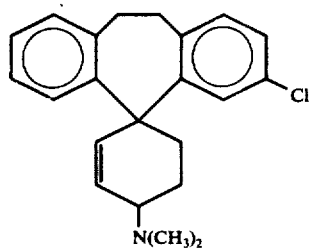

or a pharmaceutically acceptable acid addition salt thereof.

18. A method for the treatment of neurotic conditions of different origins in man comprising administering to a person suffering from such condition of a therapeutically effective amount for the relief of neurosis of a compound having the formula

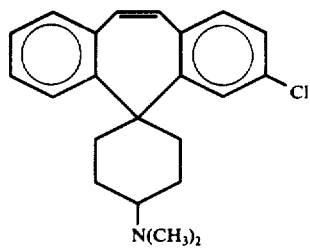

VII

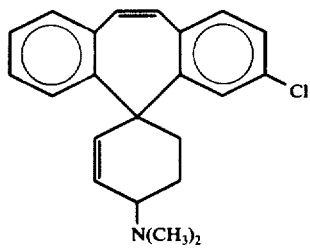

VIII

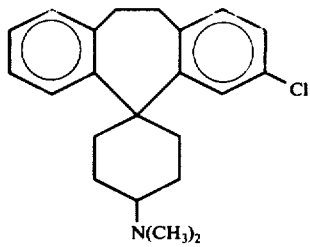

IX

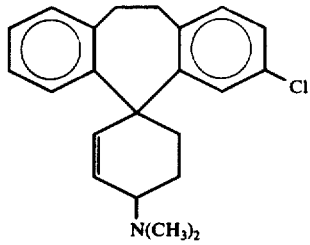

X or a therapeutically acceptable acid addition salt thereof.

19. The method as described in claim 18 wherein the compound administered has the formula

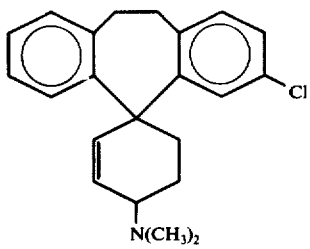

or a pharmaceutically acceptable acid salt thereof.

* * * * *